United States Patent
Nishimura et al.

(10) Patent No.: US 10,239,950 B2
(45) Date of Patent: Mar. 26, 2019

(54) ANTI-MUC1 ANTIBODY OR ANTIGEN-BINDING FRAGMENT THEREOF AND USES THEREOF

(71) Applicant: MEDICINAL CHEMISTRY PHARMACEUTICALS, CO., LTD., Hokkaido (JP)

(72) Inventors: Shinichiro Nishimura, Hokkaido (JP);
Risho Miyoshi, Hokkaido (JP);
Kentaro Naruchi, Hokkaido (JP);
Masakazu Tanaka, Hokkaido (JP);
Masaharu Sato, Hokkaido (JP)

(73) Assignee: MEDICINAL CHEMISTRY PHARMACEUTICALS, Co., Ltd., Hokkaido (JP)

( * ) Notice: Subject to any disclaimer, the term of this patent is extended or adjusted under 35 U.S.C. 154(b) by 133 days.

(21) Appl. No.: 15/306,942

(22) PCT Filed: Apr. 28, 2015

(86) PCT No.: PCT/JP2015/062761
§ 371 (c)(1),
(2) Date: Oct. 26, 2016

(87) PCT Pub. No.: WO2015/166934
PCT Pub. Date: Nov. 5, 2015

(65) Prior Publication Data
US 2017/0198056 A1    Jul. 13, 2017

(30) Foreign Application Priority Data

Apr. 28, 2014 (JP) .................... 2014-092299

(51) Int. Cl.
| | |
|---|---|
| *C07K 16/00* | (2006.01) |
| *C07K 16/30* | (2006.01) |
| *G01N 33/574* | (2006.01) |
| *C07K 16/28* | (2006.01) |
| *C12Q 1/02* | (2006.01) |

(52) U.S. Cl.
CPC ...... *C07K 16/3092* (2013.01); *C07K 16/2896* (2013.01); *G01N 33/574* (2013.01); *G01N 33/57492* (2013.01); *C07K 2317/33* (2013.01); *C07K 2317/34* (2013.01); *C07K 2317/73* (2013.01); *C07K 2317/76* (2013.01); *C12Q 1/02* (2013.01); *G01N 2333/70596* (2013.01); *G01N 2400/02* (2013.01)

(58) Field of Classification Search
None
See application file for complete search history.

(56) References Cited

U.S. PATENT DOCUMENTS

2006/0292643 A1   12/2006 Goletz et al.

FOREIGN PATENT DOCUMENTS

| | | |
|---|---|---|
| DK | 2008-040362 | 4/2008 |
| JP | H02-503387 | 10/1990 |
| JP | 3698370 | 6/1995 |
| JP | 2002-502621 | 1/2002 |
| JP | 2003-519096 | 6/2003 |
| JP | 2006-111618 | 4/2006 |
| JP | 2010-505775 | 2/2010 |
| WO | 1993/20841 | 10/1993 |
| WO | 2010/050528 | 5/2010 |
| WO | 2011/135869 | 11/2011 |

OTHER PUBLICATIONS

Granziero et al, Eur. J. Immunol. 1999, 29:1127-1138.*
Byers, T., CA Journal, vol. 49, No. 6, Nov./Dec. 1999.*
Extended European Search Report dated Dec. 6, 2017 for EP Nat. Phase of PCT/JP2015/062711; EP App. No. 15785665.9.
Beatson et al. MUC1 immunotherapy. Immunotherapy. (2010) 2(3):305-327.
Engelmann et al. Identification and topology of variant sequences within individual repeat domains of the human epithelial tumor mucin MUC1. J. Biol. Chem. (2001) 276(30):27764-27769.
Bafna et al. Membrane-bound mucins: the mechanistic basis for alterations in the growth and survival of cancer cells. Oncogene. (2010) 29(20):2893-2904.
Remmers et al. Aberrant expression of mucin core proteins and o-linked glycans associated with progression of pancreatic cancer. Clin Cancer Res. (2013) 19(8):1981-1993.
Liu et al. Galectins as modulators of tumour progression. Nature Rev Cancer. (2005) 5(1)29-41.
Danielczyk et al. PankoMab: a potent new generation anti-tumour MUC1 antibody. Cancer Immunol Immunother. 559(11):1337-1347.
Cao et al. Binding patterns of 51 monoclonal antibodies to peptide and carbohydrate epitopes of the epithelial mucin (MUC1) on tissue sections of adenolymphomas of the parotid (Warthin's tumours): role of epitope masking by glycans. Histochem Cell Biol. (2001) 115(4):349-356.
Ohyabu et al. An essential epitope of anti-MUC1 monoclonal antibody KL-6 revealed by focused glycopeptide library. J Am Chem Soc. (2009) 131(47):17102-17109.

(Continued)

*Primary Examiner* — Mark Halvorson
(74) *Attorney, Agent, or Firm* — Robert C. Netter, Jr.; Dann, Dorfman, Herrell & Skillman

(57) ABSTRACT

The present invention provides: an antibody exhibiting specificity for MUC1, the antibody having a glycan structure expressed at high levels in cancer cells; a method for manufacturing this antibody; and a novel means and method for the diagnosis and prevention and/or treatment of cancer using this antibody. The present invention is a monoclonal antibody to human MUC1, wherein the antibody specifically recognizes a glycopeptide having a human MUC1 tandem unit and furthermore having an O-linked glycan core (0(Tn)) in any one of the threonine and serine in the amino acid sequence of this human MUC1 tandem unit. A method for detecting MUC1 in a human body-fluid sample. A kit including this monoclonal antibody. A pharmacological composition for the prevention and/or treatment of a malignant tumor, the pharmacological composition containing this monoclonal antibody as an active ingredient.

18 Claims, 9 Drawing Sheets

Specification includes a Sequence Listing.

(56) References Cited

OTHER PUBLICATIONS

Matsushita et al. A straightforward protocol for the preparation of high performance microarray displaying synthetic MUC1 glycopeptides. Biochim Biophy Acta. (2014) 1840(3):1105-1116.

Hashimoto et al. An efficient approach for the characterization of mucin-type glycopeptides: the effect of O-glycosylation on the conformation of synthetic mucin peptides. Chemistry. (2011) 17(8):2393-2404.

Yu et al. Galectin-3 interaction with Thomsen-Friedenreich disaccharide on cancer-associated MUC1 causes increased cancer cell endothelial adhesion. J Biol Chem. (2007) 282(1):773-781.

Barresi et al. The immunoexpression of Tn, sialyl-Tn and T antigens in chronic active gastritis in relation to Helicobacter pylon infection. Pathology. (2001) 33(3):298-302.

Pinho et al. Biological significance of cancer-associated sialyl-Tn antigen: modulation of malignant phenotype in gastric carcinoma cells. Cancer Lett. (2007) 249(2):157-170.

Madsen et al. Potential for novel MUC1 glycopeptide-specific antibody in passive cancer immunotherapy. Immunopharmacol Immunotoxicol. (2013) 35(6):649-652.

International Search Report and Written Opinion issued in PCT/JP2015/062761.

International Preliminary Report on Patentability issued in PCT/JP2015/062761.

English version of International Preliminary Report on Patentability issued in PCT/JP2015/062761.

Rangappa, S., et al. "Effects of the multiple O-glycosylation states on antibody recognition of the immunodominant motif in MUC1 extracellular tandem repeats" Med. Chem. Commun. (2016) 7(6):1102-1122.

European Patent Office, Office Action dated Nov. 15, 2018 issued in the corresponding European patent application No. 15785665.9.

\* cited by examiner

SN-101
Fig. 4A) Microarray arrangement
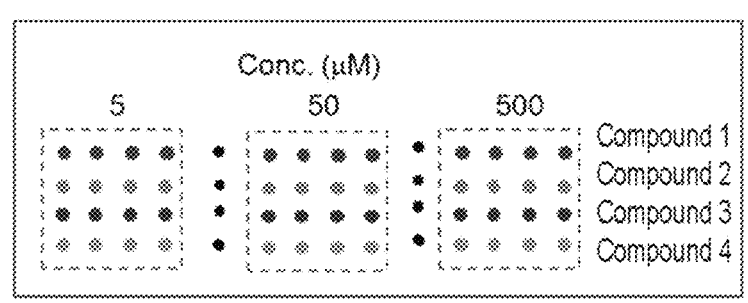
Fig. 4B) Microarray image
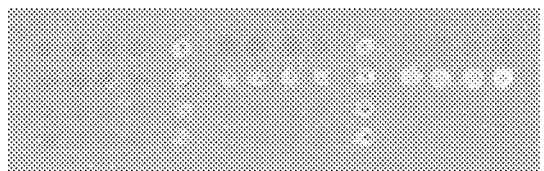
Fig. 4C) Fluorescence strength
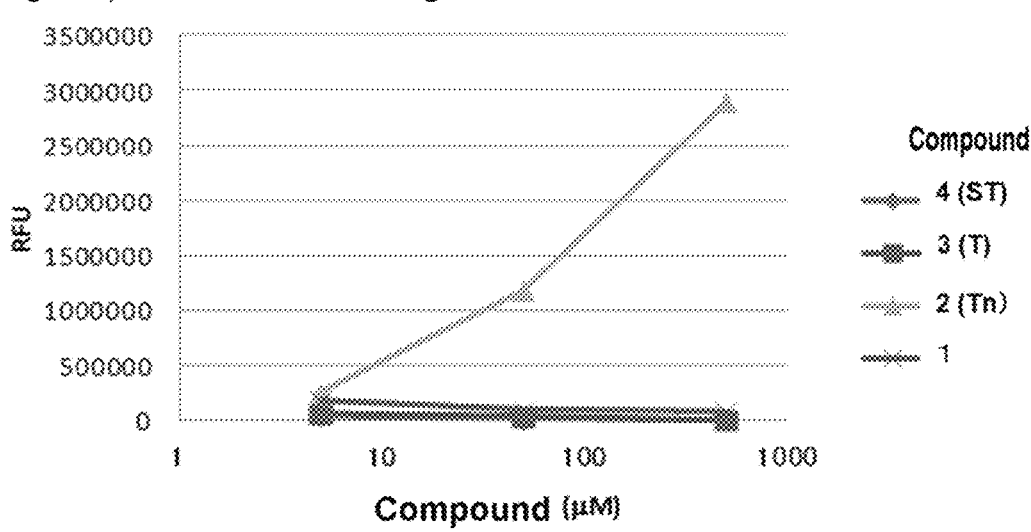

Fig. 7

Amino acid sequence of antibody variable region

[Z1] SN-101 H chain variable region

```
                      CDR1                    CDR2
  1 EVNLEESGGGLVQPGGSMKLSCVASGFTFSNYWMNWVRQSPEKGLEWVAQIRLKSDNYAT  60
                                           CDR3
 61 HYAESVKGRFTISRDDSKSSVYLQMNNLRAEDTGIYYCTGGVFDYWGQGTTLTVSS      116
```

[Z2] SN-101 L chain variable region

```
                              CDR1                    CDR2
  1 DVVMTQTPLSLPVSLGDQASISCRSSQSLVHSNGNTYLHWYLQKPGQSPKLLIYKVSNRF  60
 61 SGVPDRFSGSGSGTDFTLKISRVEAEDLGVYFCSQSTHVPPWTFGGGTKLEIK         113
```

[Z3] SN-102 H chain variable region

```
                      CDR1                    CDR2
  1 EVQLQQSGAELVKPGASVKLSCTASGFNIKDYYMHWVKQRTEQGLEWIGRIDPEDGETKY  60
                                           CDR3
 61 APKFQGKAIITADTSSNTAYLQLSSLTSEDTAVYYCVHFYYGYDVGRGYWGQGTTLTVSS  120
```

[Z4] SN-102 L chain variable region

```
                      CDR1                    CDR2
  1 DIVMSQSPSSLAVSVGEKVTMSCKSSQSLLYSSNQKNYLAWYQQKPGQSPKLLIYWASTR  60
                                           CDR3
 61 ESGVPDRFTGSGSGTDFTLTISSVKAEDLAVYYCQQYYSYTFGGGTKLEIK            111
```

SF0075 mouse IgG1 heavy chain

```
  1 ATGGACTTGAGACTGAGCTGTGCTTTTATTATTGTTCTTTTAAAAGGGGTCCAGAGTGAA    60
    M  D  L  R  L  S  C  A  F  I  I  V  L  L  K  G  V  Q  S  E

61 GTGAACCTTGAGGAGTCTGGAGGAGGCTTGGTACAACCTGGAGGATCCATGAAACTCTCC   120
    V  N  L  E  E  S  G  G  G  L  V  Q  P  G  G  S  M  K  L  S
                                           CDR1
121 TGTGTTGCCTCTGGATTCACTTTCAGTAACTACTGGATGAACTGGGTCCGCCAGTCTCCA   180
    C  V  A  S  G  F  T  F  S |N  Y  W  M  N| W  V  R  Q  S  P
                              CDR2
191 GAGAAGGGGCTTGAGTGGGTTGCTCAAATTAGATTGAAATCTGATAATTATGCAACACAT   240
    E  K  G  L  E  W  V  A |Q  I  R  L  K  S  D  N  Y  A  T  H

241 TATGCGGAGTCTGTGAAAGGGAGGTTCACCATCTCAAGAGATGATTCCAAAAGTAGTGTC   300
    Y  A  E  S  V  K  G| R  F  T  I  S  R  D  D  S  K  S  S  V
                                                         CDR3
301 TACCTGCAAATGAACAACTTAAGGGCTGAAGACACTGGAATTTATTACTGCACAGGCGGG   360
    Y  L  Q  M  N  N  L  R  A  E  D  T  G  I  Y  Y  C  T  G |G

361 GTCTTTGACTACTGGGGCCAAGGCACCACTCTCACAGTCTCCTCAGCCAAAACGACACCC   420
    V  F  D  Y| W  G  Q  G  T  T  L  T  V  S  S  A  K  T  T  P

421 CCATCTGTCTATCCACTGGCCCCTGGATCTGCTGCCCAAACTAACTCCATGGTGACCCTG   480
    P  S  V  Y  P  L  A  P  G  S  A  A  Q  T  N  S  M  V  T  L

481 GGATGCCTGGTCAAGGGCTATTTCCCTGAGCCAGTGACAGTGACCTGGAACTCTGGATCC   540
    G  C  L  V  K  G  Y  F  P  E  P  V  T  V  T  W  N  S  G  S
```

SF0075 mouse Igκ light chain

```
  1 ATGAAGTTGCCTGTTAGGCTGTTGGTGCTGATGTTCTGGATTCCTGCTTCCAGCAGTGAT    60
    M  K  L  P  V  R  L  L  V  L  M  F  W  I  P  A  S  S  S  D

61 GTTGTGATGACCCAAACTCCACTCTCCCTGCCTGTCAGTCTTGGAGATCAAGCCTCCATC   120
    V  V  M  T  Q  T  P  L  S  L  P  V  S  L  G  D  Q  A  S  I
                       CDR1
121 TCTTGCAGATCTAGTCAGAGCCTTGTACACAGTAATGGAAACACCTATTTACATTGGTAC   180
    S  C |R  S  S  Q  S  L  V  H  S  N  G  N  T  Y  L  H| W  Y
                                                CDR2
191 CTGCAGAAGCCAGGCCAGTCTCCAAAGCTCCTGATCTACAAAGTTTCCAACCGATTTTCT   240
    L  Q  K  P  G  Q  S  P  K  L  L  I  Y |K  V  S  N  R  F  S

241 GGGGTCCCAGACAGGTTCAGTGGCAGTGGATCAGGGACAGATTTCACACTCAAGATCAGC   300
    G  V  P  D  R  F  S  G  S  G  S  G  T  D  F  T  L  K  I  S
                                      CDR3
301 AGAGTGGAGGCTGAGGATCTGGGAGTTTATTTCTGCTCTCAAAGTACACATGTTCCTCCG   360
    R  V  E  A  E  D  L  G  V  Y  F  C |S  Q  S  T  H  V  P  P

361 TGGACGTTCGGTGGAGGCACCAAGCTGGAAATCAAACGGGCTGATGCTGCACCAACTGTA   420
    W  T| F  G  G  G  T  K  L  E  I  K  R  A  D  A  A  P  T  V

421 TCCATCTTCCCACCATCCAGTGAGCAGTTAACATCTGGAGGTGCCTCAGTCGTGTGCTTC   480
    S  I  F  P  P  S  S  E  Q  L  T  S  G  G  A  S  V  V  C  F

481 TTGAACAACTTCTACCCCAAAGACATCAATGTCAAGTGGAAGATTGATGGCAGTGAACGA   540
    L  N  N  F  Y  P  K  D  I  N  V  K  W  K  I  D  G  S  E  R
```

Fig.9-1

```
           10         20         30         40         50         60
ATGAAATGCAGCTGGATCATCTTCTTCCTGATGGCAGTGGTTACAGGGGTCAATTCAGAG
 M  K  C  S  W  I  I  F  F  L  M  A  V  V  T  G  V  N  S  E 70         80         90        100        110        120
GTTCAGCTGCAGCAGTCTGGGGCAGAGCTTGTGAAGCCAGGGGCCTCAGTCAAGTTGTCC
 V  Q  L  Q  Q  S  G  A  E  L  V  K  P  G  A  S  V  K  L  S

CDR1
          130        140    150        160        170        180
TGCACAGCTTCTGGCTTCAACATTAAAGACTACTATATGCACTGGGTGAAGCAGAGGACT
 C  T  A  S  G  F  N  I  K |D  Y  Y  M  H| W  V  K  Q  R  T

CDR2
          190        200        210        220       230        240
GAACAGGGCCTGGAGTGGATTGGAAGGATTGATCCTGAGGATGGTGAAACTAAATATGCC
 E  Q  G  L  E  W  I  G |R  I  D  P  E  D  G  E  T  K  Y  A 250        260        270        280        290        300
CCGAAATTCCAGGGCAAGGCCATTATAACAGCAGACACATCCTCCAACACAGCCTACCTG
 P  K  F  Q  G| K  A  I  I  T  A  D  T  S  S  N  T  A  Y  L 310        320        330        340        350        360
CAGCTCAGCAGCCTGACATCTGAGGACACTGCCGTCTATTACTGTGTTCACTTCTACTAT
 Q  L  S  S  L  T  S  E  D  T  A  V  Y  Y  C  V  H |F  Y  Y

CDR3
         370        380        390        400        410        420
GGTTACGACGTAGGTCGAGGCTACTGGGGCCAAGGCACCACTCTCACAGTCTCCTCAGCC
 G  Y  D  V  G  R  G  Y| W  G  Q  G  T  T  L  T  V  S  S  A 430        440        450        460        470        480
AAAACGACACCCCCATCTGTCTATCCACTGGCCCCTGGATCTGCTGCCCAAACTAACTCC
 K  T  T  P  P  S  V  Y  P  L  A  P  G  S  A  A  Q  T  N  S 490        500        510        520        530        540
ATGGTGACCCTGGGATGCCTGGTCAAGGGCTATTTCCCTGAGCCAGTGACAGTGACCTGG
 M  V  T  L  G  C  L  V  K  G  Y  F  P  E  P  V  T  V  T  W 550        560        570        580        590        600
AACTCTGGATCCCTGTCCAGCGGTGTGCACACCTTCCCAGCTGTCCTGCAGTCTGACCTC
 N  S  G  S  L  S  S  G  V  H  T  F  P  A  V  L  Q  S  D  L 610        620        630        640        650        660
TACACTCTGAGCAGCTCAGTGACTGTCCCCTCCAGCACCTGGCCCAGCCAGACCGTCACC
 Y  T  L  S  S  S  V  T  V  P  S  S  T  W  P  S  Q  T  V  T 670        680        690        700        710        720
TGCAACGTTGCCCACCCGGCCAGCAGCACCAAGGTGGACAAGAAAATTGGATCCAAGGGC
 C  N  V  A  H  P  A  S  S  T  K  V  D  K  K  I  G  S  K  G

730
GAATTC
 E  F
```

SN-102 H chain variable region and a part of constant region

: H chain variable region
　　□ : CDR region

Fig.9-2

```
         10        20        30        40        50        60
ATGGATTCACAGGCCCAGGTTCTTATGTTACTGCTGCTATGGGTATCTGGTACCTGTGGG
 M  D  S  Q  A  Q  V  L  M  L  L  L  W  V  S  G  T  C  G 70        80        90       100       110       120
GACATTGTGATGTCACAGTCTCCATCCTCCCTAGCTGTGTCAGTTGGAGAGAAGGTTACT
 D  I  V  M  S  Q  S  P  S  S  L  A  V  S  V  G  E  K  V  T

CDR1
        130       140       150       160       170       180
ATGAGCTGCAAGTCCAGTCAGAGCCTTTTATATAGTAGCAATCAAAAGAACTACTTGGCC
 M  S  C |K  S  S  Q  S  L  L  Y  S  S  N  Q  K  N  Y  L  A

CDR2
        190       200       210       220       230       240
TGGTACCAGCAGAAACCAGGGCAGTCTCCTAAACTGCTGATTTACTGGGCATCCACTAGG
 W  Y  Q  Q  K  P  G  Q  S  P  K  L  L  I  Y |W  A  S  T  R 250       260       270       280       290       300
GAATCTGGGGTCCCTGATCGCTTCACAGGCAGTGGATCTGGGACAGATTTCACTCTCACC
 E  S| G  V  P  D  R  F  T  G  S  G  S  G  T  D  F  T  L  T

CDR3
        310       320       330       340       350       360
ATCAGCAGTGTGAAGGCTGAAGACCTGGCAGTTTATTACTGTCAGCAATATTATAGCTAC
 I  S  S  V  K  A  E  D  L  A  V  Y  Y  C |Q  Q  Y  Y  S  Y 370       380       390       400       410       420
ACGTTCGGAGGGGGGACCAAGCTGGAAATAAAACGGGCTGATGCTGCACCAACTGTATCC
 T| F  G  G  G  T  K  L  E  I  K  R  A  D  A  A  P  T  V  S 430       440       450       460       470       480
ATCTTCCCACCATCCAGTGAGCAGTTAACATCTGGAGGTGCCTCAGTCGTGTGCTTCTTG
 I  F  P  P  S  S  E  Q  L  T  S  G  G  A  S  V  V  C  F  L 490       500       510       520       530       540
AACAACTTCTACCCCAAAGACATCAATGTCAAGTGGAAGATTGATGGCAGTGAACGACAA
 N  N  F  Y  P  K  D  I  N  V  K  W  K  I  D  G  S  E  R  Q 550       560       570       580       590       600
AATGGCGTCCTGAACAGTTGGACTGATCAGGACAGCAAAGACAGCACCTACAGCATGAGC
 N  G  V  L  N  S  W  T  D  Q  D  S  K  D  S  T  Y  S  M  S 610       620       630       640       650       660
AGCACCCTCACGTTGACCAAGGACGAGTATGAACGACATAACAGCTATACCTGTGAGGCC
 S  T  L  T  L  T  K  D  E  Y  E  R  H  N  S  Y  T  C  E  A 670       680       690       700       710       720
ACTCACAAGACATCAACTTCACCCATTGTCAAGAGCTTCAACAGGAATGAGTGTTAG
 T  H  K  T  S  T  S  P  I  V  K  S  F  N  R  N  E  C  *
```

SN-102 L chain variable region and a part of constant region

: H chain variable region
 ☐ : CDR region

ANTI-MUC1 ANTIBODY OR ANTIGEN-BINDING FRAGMENT THEREOF AND USES THEREOF

TECHNICAL FIELD

The present application is § 371 application of PCT/JP2015/062761 filed Apr. 28, 2015 which claims priority to JP Patent Application No. 2014-092299 filed Apr. 28, 2014, the entire disclosure of each being incorporated by reference herein.

CROSS-REFERENCE TO RELATED APPLICATIONS

This application claims benefit of priority to Japanese Patent Application No. 2014-92299 filed on Apr. 28, 2014, which is expressly incorporated herein by reference in its entirety.

BACKGROUND ART

MUC1 is a type of mucin glycoprotein. It comprises the core protein coded for by the MUC1 gene (MUC1) and numerous sugar chains that are bonded to the core-protein by O-type sugar chain bonds. Mucin comes in the form of secretory mucin that is produced by epithelial cells and the like, and membrane-bound mucin that comprises a hydrophobic transmembrane portion and is bound to the cellular membrane. MUC1 is a membrane-bound mucin of epithelial cells that is present in normal cells on the distal end surface of mammary gland cells and in milk fat droplets, and in a number of glandular epithelial cells, such as in the pancreas and kidneys (Nonpatent Reference 1). Its molecular size is greater than or equal to 400 kDa, of which 50% is comprised of O-bond-type sugar chains. This glycoprotein is comprised of a short N-terminal region, a central region comprised of tandem repeats 25% of which are accounted for by amino acids having hydroxyl groups, a transmembrane region comprised of 31 amino acids, and a short C-terminal region on the cytoplasm side. The extracellular region containing the central region is severed and released under various conditions. Each tandem repeat (tandem unit) is comprised of 20 amino acids (Pro-Asp-Thr-Arg-Pro-Ala-Pro-Gly-Ser-Thr-Ala-Pro-Pro-Ala-His-Gly-Val-Thr-Ser-Ala) having five sites that can be modified by O-sugar chains. The number of tandem repeats varies between 20 to 125 by allele, so this region is referred to as a variable number of tandem repeats (VNTR). The VNTR region undergoes size polymorphism in which the number of repeats that is expressed varies genetically by individual. Four types of sequence polymorphs are known based on the genetic mutation of specific amino acids. Within this sequence polymorphism, the frequency of the mutation from Pro-Asp-Thr-Arg (PDTR) to Pro-Glu-Ser-Arg (PESR) is high (Nonpatent Reference 2).

MUC1 is known to be overexpressed in many cancers, such as breast cancer, prostate cancer, hepatocellular carcinoma, pancreatic cancer, colon cancer, and ovarian cancer. In particular, overexpression of 90% or more is observed in breast cancer, ovarian cancer, and pancreatic cancer. Further, heightened expression of MUC1 accompanies an adverse prognosis of various cancers, with the concentration of free MUC1 in the blood rising in cancer patients (Nonpatent Reference 1).

The sugar that is initially transferred by O-sugar chain modification to the serine and threonine residues of the VNTR regions of MUC1 with the greatest frequency is GalNAc (sometimes denoted as Tn). As a result, Tn antigen is produced. Although Tn is rarely seen in normal MUC1, it is found in cancer-derived MUC1. Next, sialic acid, galactose, or GlcNAc is added to the Tn, producing sialyl-Tn (STn), core 1 (T), or core 2. When sialic acid is added to core 2, sialyl T (ST) is produced. Other sugar chains are not further added to STn, but GlcNAc and GalNAc are transferred to Tn. In cancer cells, O-type sugar chains are incompletely processed, causing expression of the sugar antigens Tn (GalNAc α-1-Ser/Thr), STn (Sia α2-6 GalNAc α-1-O-Ser/Thr), T (Gal β1-3GalNAc α-1-O-Ser/Thr), core 2 (GlcNAc β1-3GalNAc α1-O-Ser/Thr), ST (Sia α2-3Bal β1-3GalNac α1-O-Ser/THR/Sia α2-6(Gal β1-3)GalNAc α1-O-Ser/Thr) that are common in cancers. As the cancer progresses, the antigen structure (epitope) changes due to different sugar chain modification such as of the five sites in the tandem repeats of MUC1 that are modifiable with 0-sugar chains (Nonpatent Reference 4). Multiple core structures are known for the O-glycan to which GalNAc is initially transferred and numbers have been assigned. The core structures of cores 0, 1, and 2 are given below:

Core 0 (Tn antigen): GalNAc
Core 1 (T antigen): Galβ1-3GalNAc
Core 2: Galβ1-3(GlcNAcβ1-6) GalNAc The addition of a sugar chain by O-glycosylation of the MUC1 protein plays important roles in the protection of the epithelial cell layer, immune response, cell attachment, and inflammatory response, as well as in cancerization and cancer metastasis. A relation has been reported between the overexpression of MUC1 due to cancerization and the dramatic change of O-glycosylation on the one hand and cancerization and cancerous metastasis on the other. Further, research and development into monoclonal antibodies to MUC1 as diagnostic drugs and treatment drugs for breast cancer and ovarian cancer is advancing (Nonpatent Reference 1). Recently, the interaction between MUC glycoprotein and galectin has been found to be important to cancer progression and metastasis (Nonpatent Reference 5).

Numerous monoclonal antibodies to purified MUC1 and synthetic peptides and glycopeptides derived from MUC1 have been reported (Patent References 1 to 5, Nonpatent References 6 and 7). The minimum sequence recognition of most of these antibodies is thought to lie in the Ala-Pro-Thr-Arg-Pro-Ala-Pro among the peptides in the tandem repeats of MUC1. The threonine that is contained in this sequence is considered to be heavily O-glycosylated, and is thus thought to have an effect on the selectivity and affinity of antibodies binding MUC1. However, for all of the monoclonal antibodies in the above reports, even when a difference based on the presence or absence of sugar chain bonds in the peptides making up the epitope has been identified, no difference has been identified in the sugar chain structure. Thus, cancer cell selectivity has been inadequate. By contrast, the present inventors have prepared antibodies with a high cross-reactivity rate with normal tissue-associated structures relative to the cancer-related structure STn of MUC1 (Patent References 6 and 7). However, even these antibodies have difficulty in accurately recognizing differences in various sugar chain peptide structures in the form of the O-glycosylated core peptides and core peptide structures of MUC1.

Patent Reference 1: JP Patent No. 3698370
Patent Reference 2: JP-A-2002-502621
Patent Reference 3: JP-A-2003-519096
Patent Reference 4: US-A-2006/0292643
Patent Reference 5: JP-A-2010-505775
Patent Reference 6: WO2010/050528

Patent Reference 7: WO2011/135869
Patent Reference 8: JP-A-2006-111618
Nonpatent Reference 1: Beatson et al., Immunotherapy 2: 305-327 (2010)
Nonpatent Reference 2: Engelmann et al., J. Biol. Chem. 276: 27764-27769 (2001)
Nonpatent Reference 3: Bafina et al., Oncogene 29: 2893-2904 (2010)
Nonpatent Reference 4: Clin. Cancer Res. 19: 1981-1983 (2013)
Nonpatent Reference 5: Liu et al., Nature Rev Cancer 5:29-41 (2005)
Nonpatent Reference 6: Danielczyk et al., Cancer Immunol. Immunother. 55: 1337-1347 (2006)
Nonpatent Reference 7: Cao et al., Histochem. Cell Biol. 115:349-356 (2001)
Nonpatent Reference 8: Ohyabu et al., J. Am. Chem. Soc. 131: 17102-17109 (2009)
Nonpatent Reference 9: Matsusita et al., Biochim. Biophy. Acta 1840: 1105-1116 (2014)
Nonpatent Reference 10: Hashimoto et al., Chem. Eur. J. 17: 2393-2404 (2011)
Nonpatent Reference 11: Lu-Gang et al., J. Biol. Chem. 282: 773-781 (2007)
Patent References 1 to 8 and nonpatent References 1 to 11 are expressly incorporated herein by reference in its entirety.

SUMMARY OF THE INVENTION

Problem to be Solved by the Invention

The present inventors have developed high-sensitivity, high-performance glycopeptide immobilized microarrays that are capable of accurately implementing epitope mapping and specific analysis of antibodies, and have established a new method of determining the true epitope structure. Using this method, they conducted epitope analysis of the above seven existing anti-MUC1 antibodies. As a result, they found that none of these antibodies was able to recognize differences in the core peptide structure of MUC1 or in O-glycosylated glycopeptide structures in core peptides (Nonpatent References 8 and 9).

The present inventors further demonstrated by NMR that in the epitope regions of anti-MUC1 antibodies, a conformation change is induced in the main chain peptide in a manner specific to the structure of the sugar chain bound to the side chain. They also clarified that the peptide conformation is sensitively changed by sugar chain modification with specific amino acid residues, and that this defines the antigen structure of the anti-MUC1 antibody (Nonpatent Reference 8). They also analyzed changes in the three-dimensional structure of mucin-derived synthetic glycopeptides by MS and NMR. On that basis, they determined that the conformation of glycopeptides was affected by sugar chain modification of the several threonine residues present in the peptide, and that sugar chain modification at specific positions imparted stable conformation of the peptide main chain (Nonpatent Reference 10).

Based on this knowledge, the present invention has for its object to provide an anti-MUC1 antibody that is specific to glycopeptides having O-bond-type sugar chains that are highly expressed in cancer cells. Here, the phrase "specific to glycopeptides having O-bond-type sugar chains" means capable of accurately recognizing differences in the various glycopeptide structures of O-glycosylated core peptides and the core peptide structure of MUC1.

A further object of the present invention is to provide a synthetic glycopeptide serving as an antigen suited to the fabrication of this antibody. A still further object of the present invention is to provide a new means and method of diagnosing, preventing, and/or treating cancer with this antibody.

The present inventors applied the new technical knowledge they had gleaned about sugar chains and glycopeptides to achieving the above objects. They artificially synthesized the glycopeptide comprising Tn that constitutes the core sugar structure that is initially transferred by O-sugar chain modification to the serine and threonine residues in the VNTR regions of MUC1, and employed this artificially synthesized glycopeptide as antigen to fabricate monoclonal antibodies. For a number of the anti-MUC1 antibodies that were obtained from glycopeptides comprising Tn (also referred to as "Tn antigens" hereinafter), they employed a microarray loaded with glycopeptides derived from the VNTR regions of various mucins containing the glycopeptides employed as antigens to analyze antibody specificity, and examined the characteristics of the antibodies. They also examined these antibodies in terms of binding to and accumulating the MUC1 expressed by various cancer cells, reacting to cancer patient serum, effect in inhibiting the proliferation of cancer cells, and effect in inhibiting metastatis. As a result of this examination, they discovered antibodies that were capable of accurately recognizing differences in the core peptide structure of MUC1 and various glycopeptide structures produced by the O-glycosylation of core peptides. The present invention has been devised on that basis.

Means of Solving the Problem

The present invention is as set forth below.
[1]
A monoclonal antibody to human MUC1, or an antigen-binding fragment thereof, specifically recognizing human MUC1 tandem units and glycopeptides having a O-bond-type sugar chain core 0 (Tn) on any of the threonines or the serines in the amino acid sequence of the human MUC1 tandem units.
[2]
The monoclonal antibody or antigen-binding fragment thereof according to [1], wherein the amino acid sequence of the human MUC1 tandem unit comprises the amino acid sequence shown by SEQ ID NO: 1, and the O-bond-type sugar chain core 0 (Tn) binds to the position eight threonine in the amino acid sequence denoted by SEQ ID NO: 1.
[3]
The monoclonal antibody or antigen-binding fragment thereof according to [1], wherein the amino acid sequence of the human MUC1 tandem unit comprises the amino acid sequence shown by SEQ ID NO: 2, and the O-bond-type sugar chain core 0 (Tn) binds to the position eight serine in the amino acid sequence denoted by SEQ ID NO: 2.
[4]
The monoclonal antibody or antigen-binding fragment thereof according to any one of [1] to [3], having the binding characteristics given by i) to iii) below:
i) not binding to a glycopeptide in which the O-bond-type sugar chain core 0 (Tn) has been substituted with a O-bond-type sugar chain T or STn;
ii) not binding to the peptide comprising the amino acid sequence shown by SEQ ID NO: 3 (naked peptide); and iii) not binding to a glycopeptide in which Tn has been modified in the tandem unit peptide of MUC2 or the tandem unit peptide of MUC4.

[5]
The monoclonal antibody or antigen-binding fragment thereof according to any one of [1] to [4], comprising at least one antigen-binding portion comprising an immunoglobulin heavy chain variable region (VH) domain and an immunoglobulin light chain variable region (VL) domain, with the heavy chain variable region domain comprising in the sequence thereof complementarity determining regions CDR1, CDR2, and CDR3, with CDR1 being comprised of the amino acid sequence shown by SEQ ID NO: 8, CDR2 being comprised of the amino acid sequence of SEQ ID NO: 9, and CDR3 being comprised of the amino acid sequence shown by SEQ ID NO: 10, with the light chain variable region domain comprising in the sequence thereof complementarity determining regions CDR1', CDR2', and CDR3', with CDR1' being comprised of the amino acid sequence shown by SEQ ID NO: 11, CDR2' being comprised of the amino acid sequence of SEQ ID NO: 12, and CDR3' being comprised of the amino acid sequence shown by SEQ ID NO: 13.

[6]
The monoclonal antibody or antigen-binding fragment thereof according to any one of [1] to [4], comprising at least one antigen-binding portion comprising an immunoglobulin heavy chain variable region (VH) domain and an immunoglobulin light chain variable region (VL) domain, with the heavy chain variable region domain comprising in the sequence thereof complementarity determining regions CDR1, CDR2, and CDR3, with CDR1 being comprised of the amino acid sequence shown by SEQ ID NO: 16, CDR2 being comprised of the amino acid sequence of SEQ ID NO: 17, and CDR3 being comprised of the amino acid sequence shown by SEQ ID NO: 18, with the light chain variable region domain comprising in the sequence thereof complementarity determining regions CDR1', CDR2', and CDR3', with CDR1' being comprised of the amino acid sequence shown by SEQ ID NO: 19, CDR2' being comprised of the amino acid sequence of SEQ ID NO: 20, and CDR3' being comprised of the amino acid sequence shown by SEQ ID NO: 21.

[7]
The monoclonal antibody or antigen-binding fragment thereof according to [5], comprising a heavy chain variable region comprised of the amino acid sequence of SEQ ID NO: 6 and a light chain variable region comprised of the amino acid sequence of SEQ ID NO: 7.

[8]
The monoclonal antibody or antigen-binding fragment thereof according to [6], comprising a heavy chain variable region comprised of the amino acid sequence of SEQ ID NO: 14 and a light chain variable region comprised of the amino acid sequence of SEQ ID NO: 15.

[9]
The monoclonal antibody or antigen-binding fragment thereof according to any one of [1] to [8], wherein the antigen-binding fragment is a peptide comprising at least one from among complementarity determining regions CDR1, CDR2, CDR3, CDR1', CDR2', and CDR3'.

[10]
The monoclonal antibody or antigen-binding fragment thereof according to any one of [1] to [9], wherein the antibody-binding fragment is Fab, F(ab')2, Fab', diabody, a single-chain antibody (such as scFv or dsFv), a bispecific antibody, a chimeric antibody, or a humanized antibody.

[11]
The monoclonal antibody or antigen-binding fragment thereof according to any one of [1] to [10], for use in specific detection of MUC1.

[12]
A method for specifically detecting MUC1 in a human body fluid sample, comprising:
(a) placing the sample in contact with the monoclonal antibody or antigen-binding fragment of any one of [1] to [10]; and
(b) measuring the formation of antibody (or antigen-binding fragment thereof)—antigen complex in the sample following contact.

[13] The method according to [12], for use in determination of presence of a malignant tumor that exhibits abnormal expression of MUC1 in the body fluid sample.

[14] The method according to [13], wherein the malignant tumor is selected from the group consisting of breast cancer, prostate cancer, hepatocellular carcinoma, pancreatic cancer, colon cancer, and ovarian cancer.

[15] A kit for employing the method described in any one of [12] to [14], comprising:
(a) the monoclonal antibody or antigen-binding fragment thereof according to any one of [1] to [10]; and
(b) a reagent for measuring the antibody (or antigen-binding fragment thereof)—antigen complex.

[16]
A pharmaceutical composition for preventing or treating malignant tumors, comprising an active component in the form of the monoclonal antibody or antigen-binding fragment thereof according to any one of [1] to [10].

[17]
The composition according to [16], wherein the malignant tumor is selected from the group consisting of breast cancer, prostate cancer, hepatocellular carcinoma, pancreatic cancer, colon cancer, and ovarian cancer.

Effect of the Invention

The present invention provides an anti-MUC1 antibody in the form of a monoclonal antibody for human MUC1 that specifically recognizes MUC1 in which the O-bond-type sugar chain of the tandem unit peptide of MUC1 is core 0 (Tn), does not recognize or bind the naked peptide in which the O-bond-type sugar chain is not added or MUC1 chain peptides other than those in which the O-bond-type sugar chain is Tn, and provides a method employing an antigen glycopeptide to fabricate antibody. Using the anti-MUC1 antibody of the present invention, it is possible to specifically, highly sensitively, reliably, and conveniently detect MUC1 protein, and determine malignant tumors and inflammatory illnesses in which the expression of MUC1 changes relative to a normal control. By suppressing the progress or metastasis of cancer by means of the anti-MUC1 antibody of the present invention, it can be employed as a drug to prevent and/or treat cancer.

BRIEF DESCRIPTION OF THE DRAWING

FIGS. 4A-4D Evaluation of the reaction specificity of SN-101 and SN-102 by means of a glycopeptide-immobilized microarray.

FIG. 7 Shows an example of the amino acid sequence of the variable region of antibodies SN-101 and SN-102. [Z1] SN-101 H chain variable region, SEQ ID NO: 22; [Z2] SN-101 L chain variable region, SEQ ID NO: 23; [Z3] SN-102 H chain variable region, SEQ ID NO: 24; [Z4] SN-102 L chain variable region, SEQ ID NO: 25.

FIG. 8 Shows the amino acid sequence containing the variable region of antibody SN-101. SF00075 Mouse IgG1 heavy chain Nucleic acid (SEQ ID NO: 26); amino acid (SEQ ID NO: 27)

FIGS. 9-1 and 9-2 Shows the amino acid sequence containing the variable region of antibody SN-102. H chain variable region and a part of constant region Nucleic acid (SEQ ID NO: 30), amino acid (SEQ ID NO: 31); L chain variable region and a part of constant region Nucleic acid (SEQ ID NO: 32), amino acid (SEQ ID NO: 33).

MODES OF CARRYING OUT THE INVENTION

Figure 1A:
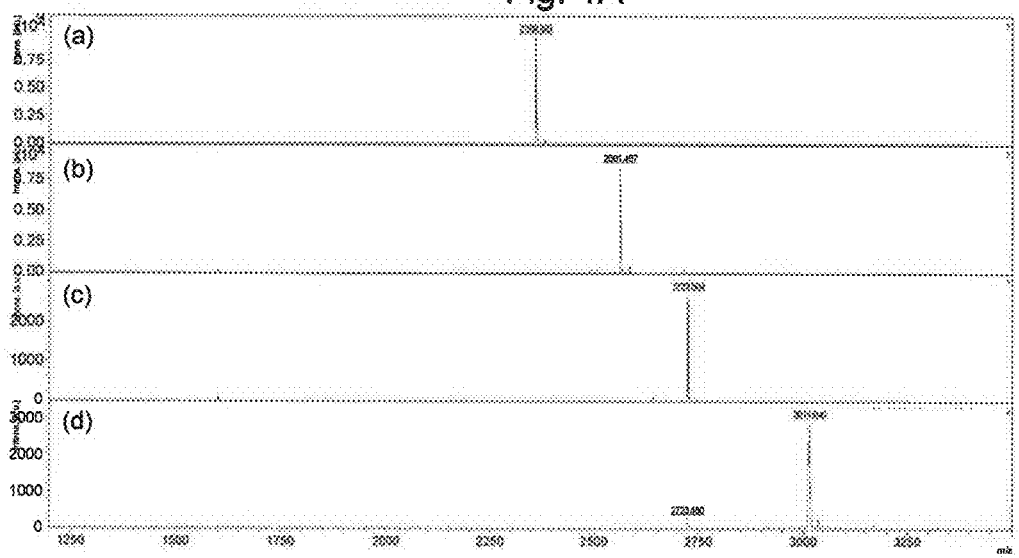
FIGS. 1A-1C A MALDI-TOFMS spectrum of MUC1-derived glycopeptides.

The present invention will be described in greater detail below.
1. Antigen Glycopeptides and Antibody The antibody of the present invention is a monoclonal antibody to human MUC1 that specifically recognizes human MUC1 tandem units and glycopeptides having a O-bond-type sugar chain core 0 (Tn) on any of the threonines or serines in the amino acid sequence of human MUC1 tandem units.

An example of the antibody of the present invention is a monoclonal antibody wherein the amino acid sequence of human MUC1 tandem units comprises the amino acid sequence shown by SEQ ID NO: 1 above and the O-bond-type sugar chain core 0 (Tn) is bonded to the position eight threonine in the amino acid sequence shown by SEQ ID NO: 1. Another example of the antibody of the present invention is a monoclonal antibody wherein the amino acid sequence of the MUC1 tandem units comprises the amino acid sequence of SEQ ID NO: 2 above and the O-bond-type sugar chain core 0 (Tn) is bonded to the position eight serine in the amino acid sequence shown by SEQ ID NO: 2.

These antibodies of the present invention can be those having the binding characteristics of i) to iii) below:
i) not binding to glycopeptides in which the O-bond-type sugar chain core 0 (Tn) has been substituted with an O-bond-type sugar chain T or STn;
ii) not binding to a peptide comprising the amino acid sequence shown by SEQ ID NO: 3 (naked peptide); and
iii) not binding to a glycopeptide in which Tn has been modified in the tandem unit peptide of MUC2 having the amino acid sequence of SEQ ID NO: 4 or in the tandem unit peptide of MUC4 having the amino acid sequence of SEQ ID NO: 5.

1-1. The Antigen Glycopeptide

The sugar that is initially transferred to the core peptide as an O-bond-type sugar chain of the MUC1 tandem repeat is most often GalNAc. As a result, Tn antigen is produced. Tn is seldom seen in normal MUC1, but is found in cancer-derived MUC1.

The tandem unit peptide of human MUC1 has the following amino acid sequence:

(SEQ ID NO: 1)
Gly-Val-Thr-Ser-Ala-Pro-Asp-Thr-Arg-Pro-Ala-Pro-Gly-Ser-Thr-Ala-Pro-Pro-Ala-His-Gly-Val-Thr.

A tandem unit peptide variant of human MUC1 has the following amino acid sequence: Gly-Val-Thr-Ser-Ala-Pro-Glu-Ser-Arg-Pro-Ala-Pro-Gly-Ser-Thr-Ala-Pro-Pro-Ala-His-Gly-Val-Thr (SEQ ID NO: 2).

In fabricating the antigen, a glycopeptide in which an O-bond-type sugar chain has been added to a prescribed amino acid of either of the above peptides can be employed as antigen. This glycopeptide to which the O-bond-type sugar chain has been added is artificially synthesized.

The O-bond-type sugar chain is a sugar chain comprising the core structure of Tn (GalNAc). The O-bond-type sugar chain binds to the threonine (Thr) or serine (Ser) that is the position eight amino acid of the tandem unit peptide having the amino acid sequence shown by SEQ ID NO: 1 or 2 above.

Synthesis of the antigen glycopeptide can be conducted by a synthesis technique highly utilizing microwaves and enzyme synthesis developed by the present inventors. More specifically, for example, it can be implemented according to the methods described in Nonpatent Reference 9 and Patent Reference 6 to 8. The complete contents of Nonpatent Reference 9 and Patent References 6 to 8 are hereby specifically incorporated by reference.

1-2. The Antibody:

The antibody of the present invention can be prepared by the usual methods using the glycopeptide described in 1-1 as antigen. The antigen glycopeptide can be bonded to a carrier protein to enhance its antigenic properties. In that case, an antigen glycopeptide in which a Cys required for binding a carrier protein has been added to the C terminal of the glycopeptide can be synthesized and employed as the antigen glycopeptide. Carrier proteins include keyhole limpet hemocyanin (KLH), bovine serum albumin (BSA), ovalbumin (OVA) and the like. Commercial kits known in this technical field are available for purchase. The antigen is administered to a mammal, such as a mouse, rabbit, or rat. Immunization is principally conducted by intravenous, subcutaneous, intraperitoneal, or footpad injection. The immunization interval is not specifically limited. Immunization can be conducted from one to five times at intervals of from several days to several weeks. The antibody-producing cells are collected for from several days to 90 days from the final immunization day. Examples of antibody-producing cells are lymphocytes, spleen cells, and peripheral blood cells. To obtain hybridomas, the antibody-producing cells are fused with myeloma cells. The generally available established cell lines of myeloma cells can be employed. Cells that have the properties of drug selectivity, not being able to grow in HAT selective medium (containing hypoxanthine, aminopterin, and thymidine) in an unfused state, and being able to exist only in a state of fusion with antibody-producing cells are desirably employed. Examples of myeloma cells are myeloma cell strains such as SP2, P3X63-Ag.8.UI(P3U I), and NS-1.

The targeted hybridomas are screened from the cells following cell fusion. For example, a cell suspension is suitably diluted with RPM-1640 medium containing bovine fetal serum or the like and sown on a microtiter plate. Selective medium (such as HAT medium) is added to each well, and the cells are subsequently cultured while suitably replacing the medium. As a result, once culturing has begun in the selective medium, the cells that grow for about 10 to 30 days can be obtained as hybridomas. The supernatant of the hybridomas is then screened with an enzyme-linked immunosorbent assay (ELISA) to determine whether antibodies reacting with MUC1 are present. Fused cell cloning is conducted by the limiting dilution method or the like to establish hybridomas that produce the targeted monoclonal antibody.

The usual cell culturing methods, ascites formation methods, or the like can be employed to collect monoclonal antibodies from the established hybridomas. The antibodies can be purified by suitably selecting a known method from among ammonium sulfate precipitation, ion exchange chromatography, gel filtration, affinity chromatography, and the like, or some combination thereof can be employed for purification.

The type of globulin of the monoclonal antibodies employed in the present invention is not specifically limited. IgG, IgM, IgA, IgE, or IgD will suffice, but IgG and IgM are desirable.

The anti-MUC1 monoclonal antibody of the present invention that is fabricated using the above hybridomas is a mouse antibody. The mouse antibody can be converted to chimeric antibodies or human antibodies by a number of known, established techniques (the conversion method will be described farther below). Chimeric antibodies and human antibodies having the same antigen specificity as the anti-mouse MUC1 monoclonal antibody of the present invention are included in the antibody of the present invention. Bispecific antibodies having the same antigen specificity as the anti-mouse MUC1 monoclonal antibody of the present invention and having a different antigen specificity are included in the antibody of the present invention.

Specific examples of the monoclonal antibody of the present invention are the monoclonal antibodies SN-101 and SN-102, which are described in the examples. Monoclonal antibody SN-101 is a monoclonal antibody that is secreted by the hybridoma cell system that was deposited as Accession Number NITE BP-01845 on 16 Apr. 2014 with the National Institute of Technology and Evaluation, Patent Microorganisms Depositary (NPMD) (2-5-8 Kazusakamatari, Kisarazu-shi, Chiba Prefecture, Japan, 292-0818, under the Budapest Treaty. Monoclonal antibody SN-102 is a monoclonal antibody that is secreted by hybridoma strain 3C10-E11 (see examples).

Monoclonal antibody SN-101 is an antibody having a heavy chain variable region comprised of the amino acid sequence of SEQ ID NO: 6 and a light chain variable region comprised of the amino acid sequence of SEQ ID NO: 7. Monoclonal antibody SN-101 comprises at least one antigen-binding site containing an immunoglobulin heavy chain variable region (VH) domain and an immunoglobulin light chain variable region (VL) domain. The heavy chain variable region domain comprises within its sequence complementarity-determining regions CDR1, CDR2, and CDR3. CDR1 is comprised of the amino acid sequence of SEQ ID NO: 8. CDR2 is comprised of the amino acid sequence of SEQ ID NO: 9. And CDR3 is comprised of the amino acid sequence of SEQ ID NO: 10. The above light chain variable region domain comprises within its sequence complementarity-determining regions CDR1', CDR2', and CDR3'. CDR1' is comprised of the amino acid sequence of SEQ ID NO: 11. CDR2' is comprised of the amino acid sequence of SEQ ID NO: 12. And CDR3' is comprised of the amino acid sequence of SEQ ID NO: 13.

Monoclonal antibody SN-102 comprises a heavy chain variable region comprised of the amino acid sequence of SEQ ID NO: 14 and a light chain variable region comprised of the amino acid sequence of SEQ ID NO: 15. Monoclonal antibody SN-102 comprises at least one antigen-binding site containing an immunoglobulin heavy chain variable region (VH) domain and an immunoglobulin light chain variable region (VL) domain. The heavy chain variable region domain comprises within its sequence complementarity-determining regions CDR1, CDR2, and CDR3. CDR1 is comprised of the amino acid sequence of SEQ ID NO: 16. CDR2 is comprised of the amino acid sequence of SEQ ID NO: 17. And CDR3 is comprised of the amino acid sequence of SEQ ID NO: 18. The above light chain variable region domain comprises within its sequence complementarity-determining regions CDR1', CDR2', and CDR3'. CDR1' is comprised of the amino acid sequence of SEQ ID NO: 19. CDR2' is comprised of the amino acid sequence of SEQ ID NO: 20. And CDR3' is comprised of the amino acid sequence of SEQ ID NO: 21.

Monoclonal antibody SN-101 has the binding characteristics given by i) to v) below:
i) binding to the MUC1-derived glycopeptide Gly-Val-Thr-Ser-Ala-Pro-Asp-(Tn)Thr-Arg-Pro-Ala-Pro-Gly-Ser-Thr-Ala-Pro-Pro-Ala-His-Gly-Val-Thr-Cys;
ii) not binding to a glycopeptide in which the Tn sugar chain of the MUC1-derived glycopeptide has been substituted with T or STn;
iii) not binding to the peptide comprising the amino acid sequence shown by SEQ ID NO: 3 (naked peptide); and
iv) not binding to a glycopeptide in which Tn has been modified in the tandem unit peptide of MUC2 having the amino acid sequence shown by SEQ ID NO: 4 or the tandem unit peptide of MUC4 having the amino acid sequence denoted by SEQ ID NO: 5.

Monoclonal antibody SN-101 also binds to the MUC1-derived glycopeptide Gly-Val-Thr-Ser-Ala-Pro-Asp-(Tn)Thr-Arg-Pro-Ala-Pro-Gly-Ser-Thr-Ala-Pro-Pro-Ala-His-Gly-Val-Thr without a C-terminal Cys, and does not bind to the peptide (naked peptide) having the amino acid sequence shown in SEQ ID NO: 1.

Monoclonal antibody SN-102 has the binding characteristics given by i) to vi) below:
i) binding to the glycopeptide Gly-Val-Thr-Ser-Ala-Pro-Asp-(Tn)Thr-Arg-Pro-Ala-Pro-Gly-Ser-Thr-Ala-Pro-Pro-Ala-His-Gly-Val-Thr in which a Tn sugar chain is bonded to the position 8 threonine of the peptide having the amino acid sequence shown in SEQ ID NO: 1;
ii) not binding to, or binding only weakly to, glycopeptides in which the Tn sugar chain of the MUC1-derived glycopeptide has been substituted with T or STn;
iii) not binding to the peptide comprising the amino acid sequence shown by SEQ ID NO: 1 (naked peptide);
iv) not binding to a glycopeptide in which Tn has been modified at the position 14 serine or position 15 threonine in the peptide having the amino acid sequence shown by SEQ ID NO: 1;
v) binding to a glycopeptide in which the Tn sugar chain has been modified at all of the threonines and serines of the peptide having the amino acid sequence shown by SEQ ID NO: 1; and
vi) not binding to a glycopeptide in which Tn has been modified in the tandem unit peptide of MUC2 or the tandem unit peptide of MUC4.

Monoclonal antibody SN-102 binds to the glycopeptide Gly-Val-Thr-Ser-Ala-Pro-Asp-(Tn)Thr-Arg-Pro-Ala-Pro-Gly-Ser-Thr-Ala-Pro-Pro-Ala-His-Gly-Val-Thr-Cys having a Cys on its C-terminal and in which a Tn sugar chain is bonded to the position 8 threonine of the peptide having the amino acid sequence of SEQ ID NO: 3, and does not bind to the peptide (naked peptide) having the amino acid sequence shown by SEQ ID NO: 3.

The present invention covers an antigen-binding fragment of the monoclonal antibody in addition to the above monoclonal antibody. The antigen-binding fragment is a peptide containing at least one from among complementarity-determining regions CDR1, CDR2, CDR3, CDR1', CDR2', and CDR3' of SN-101 or SN-102. The antigen-binding fragment is, for example, Fab, F(ab')2, Fab', diabody, or a single-chain antibody (such as scFv or dsFv). However, the antigen-binding fragment is not intended to be limited to the above. It need only be a peptide containing at least one from among complementarity-determining regions CDR1, CDR2, CDR3, CDR1', CDR2', and CDR3' of SN-101 or SN-102 that has the same binding characteristics of i) to v) above as SN-101 or the same binding characteristics of i) to vi) above as SN-102. In a chimeric antibody, human antibody, or bispecific antibody, it suffices for the immunoglobulin heavy chain variable region (VH) domain and immunoglobulin light chain variable region (VL) domain to be a peptide containing the complementarity-determining regions CDR1, CDR2, CDR3, CDR1', CDR2', and CDR3' of SN-101 or SN-102, having the same binding characteristics i) to v) as SN-101 above, or having the same binding characteristics i) to vi) as SN-102 above.

Antigen-binding fragments and fabrication methods thereof will be explained below.

[Fab, F(ab')2, Fab']
Fabrication method (1): Fabricated by digesting mouse monoclonal antibody with a prescribed enzyme and severing the disulfide bonds by a reduction treatment.
  Fab: digested with papain.
  F(ab')2: digested with pepsin.
  Fab': digested with pepsin and reduction treated with β-mercaptoethanol to sever the disulfide bonds.
Fabrication method (2): Fabricated by a protein expression technique employing a genetic recombination technique
  Fab:
    A base sequence coding for a VH (H chain variable region) and a CH1 (H chain constant region domain 1)
    A base sequence coding for a VL (L-chain variable region) and a CL (L-chain constant region)
    To cause the above two sequences to be expressed by *E. coli* and animal cells (CHO, HEK 293, insect cells), they are incorporated into an expression vector suited to the specific cell, after which the gene is introduced into the cell, and Fab is obtained by the production of a recombinant protein.
  F(ab')2, Fab':
    A base sequence coding for a VH (H chain variable region) and a CH1 (H chain constant region domain 1), and a hinge region containing cysteine for the formation of a dimer
    A base sequence coding for a VL (L-chain variable region) and a CL (L-chain constant region)
    To cause the above two sequences to be expressed by *E. coli* or animal cells (CHO, HEK 293, insect cells), they are incorporated into an expression vector suited to the specific cell, after which the gene is introduced into the cell, and F(ab')2 and Fab' are obtained by the production of recombinant proteins.

[scFv, dsFv]
Fabrication method: Fabricated by a protein expression technique employing a genetic recombination technique
  scFv:
    A base sequence coding for a VH (H-chain variable region)
    A base sequence coding for flexible amino acids such as the linker sequence: "GSSSGSSSSGSSSSGSSSS" or the like.
    A base sequence coding for a VL (L chain variable region)
    To cause expression in *E. coli* or animal cells (CHO, HEK293, insect cells) as a continuous VH-linker-VL or VL-linker-VH fused protein, it is incorporated into an expression vector suited to the specific cell, after which the gene is introduced into the cell and scFv is obtained by the production of a recombinant protein.
  dsFv:
    A base sequence coding for a VH (H chain variable region)
    A base sequence coding for a VL (L chain variable region)
    A cysteine is inserted onto the C-terminal side of VH and VH. To cause expression by *E. coli* or animal cells (CHO, HEK293, insect cells) as a continuous VH-linker-VL or VL-linker-VH fused protein, it is incorporated into an expression vector suited to the specific cell, after which the gene is introduced into the cell and dsFv is obtained by the production of a recombinant protein.

[Diabody]
Fabrication method: Fabricated by a protein expression technique employing a genetic recombination technique
(1) Base sequence coding for VH (H chain variable region) for antigen X
(2) Base sequence coding for VL (L chain variable region) for antigen X
(3) Base sequence coding for VH (H chain variable region) for antigen X
(4) Base sequence coding for VL (L chain variable region) for antigen X
(5) Base sequence coding for flexible amino acid such as linker sequence:

"GSSSGSSSSGSSSSGSSSS"

To cause the expression of VH(1)-linker(5)-VL(4) and VH(3)-linker(5)-VL(2) as a continuous fused protein in *E. coli* or animal cells (CHO, HEK293, insect cells), it is incorporated into an expression vector suited to the specific cell, after which the gene is introduced into the cell and diabody is obtained by the production of a recombinant protein.

[Chimeric Antibodies or Humanized Antibodies]
  Chimeric antibodies
Fabrication method: Fabricated by a protein expression technique employing a genetic recombination technique
    A base sequence coding for a mouse VH (H chain variable region) and human antibody H chain constant region
    A base sequence coding for a mouse VL (L chain variable region) and human antibody L chain constant region
    To cause the above two sequences to be expressed in animal cells (CHO, HEK293, insect cells), they are incorporated into an expression vector suited to the specific cell, after which the gene is introduced into the cells and chimeric antibodies are obtained by the production of recombinant proteins.
  Humanized antibody
Fabrication method: Fabricated by a protein expression technique employing a genetic recombination technique
    A base sequence coding for a humanized VH in which CDR1, CDR2, and CDR3 are inserted between the FR1, FR2, FR3, and FR4 of a human antibody variable region VH among the FR1-CDR1-FR2-CDR2-FR3-

CDR3-FR4 constituting a mouse VH (H-chain variable region) and human antibody H chain constant region A base sequence coding for a humanized VL in which CDR1, CDR2, and CDR3 are inserted between the FR1, FR2, FR3, and FR4 of a human antibody variable region VL among the FR1-CDR1-FR2-CDR2-FR3-CDR3-FR4 constituting a mouse VL (H-chain variable region) and human antibody L chain constant region To cause the above two sequences to be expressed in animal cells (CHO, HEK293, insect cells), they are incorporated into expression vectors suited to the specific cell, after which the gene is introduced into the cells and humanized antibodies are obtained by the production of recombinant proteins.

2-1. Method of Specifically Detecting MUC1 in Human Body Fluid Sample

The present invention includes a method for specifically detecting MUC1 in a human body fluid sample. This method comprises steps (a) and (b) below:

(a) placing the sample in contact with the monoclonal antibody or antigen-binding fragment of the present invention; and (b) measuring the formation of antibody (or antigen-binding fragment thereof)—antigen complex in the sample following contact.

2-2. Kit for Immunological Measurement of Human MUC1

The kit of the present invention enables use of the method for detecting human MUC1 of the present invention. It comprises:

(a) the monoclonal antibody or antigen-binding fragment of the present invention; and (b) a reagent for measuring the antibody (or antigen-binding fragment thereof)—antigen complex.

The monoclonal antibody of the present invention (also referred to as "anti-MUC1 antibody") that is employed in this kit can be immobilized on a support. The support can be any substance to which an antigen will adhere that is known to a person having ordinary skill in the art. For example, the support can be the test wells of a microtiter plate, nitrocellulose, or some other suitable membrane. Alternatively, the support can be beads or a disk (such as glass, fiberglass, latex, or a plastic material such as polystyrene or polyvinyl chloride). The support can also be magnetic particles or a fiber optic sensor.

The anti-MUC1 antibody of the present invention can be labeled with a radioisotope, enzyme, fluorescent material, luminescent material, or a metal colloid, colored latex, or the like that is visually determinable by a simple measurement method. Radioisotopes that can be used for labeling are: $^{14}C$, $^{3}H$, $^{32}P$, $^{125}I$, $^{131}I$, and the like. $^{125}I$ is particularly suitable for use. This can be bonded to the monoclonal antibody by the chloramine T method, peroxidase method, iodogen method, Bolton-Hunter method, or the like. Examples of enzymes that can be employed as labels are β-galactosidase (βGAL), alkaline phosphatase (ALP), and horse radish peroxidase (HRP). These can be bonded to the monoclonal antibody by the usual methods. Florescent materials that can be employed as labels include fluorescein, fluorescamine, fluorescein isothiocyanate, and tetramethylrhodamine isothiocyanate. Luminescent materials that can be employed as labels include: luciferin, luminol derivatives, and acridinium esters. Gold colloid and colored latex can be employed in simple detection methods.

Reagents for measuring antibody (or antigen-binding fragment thereof)—antigen complexes can be suitably determined based on the immunological detection method being employed. Known reagents capable of detecting antibody-antigen complexes that are formed when human MUC1 is contained in a human body fluid sample can be employed.

In the present invention, the term "human body fluid sample" is a material that potentially contains human MUC1, such as human blood plasma, serum, blood, urine, saliva, or a cancer tissue secretion.

Other than employing the monoclonal antibody of the present invention as antibody, the MUC1 detection method of the present invention can be implemented using conventionally known immunological measurement methods. Examples of conventionally known immunological measurement methods are the immunohistochemical staining method, immunoelectron microscopy, and immunoassays (such as enzymatic immunoassays (ELISA, EIA), fluorescent immunoassays, radioimmunoassays (RIA), immunochromatography, the immunoagglutination method, and the Western blotting method). The method for measuring the formation of antibody-antigen complex in the sample following contact in step (b) can be suitably selected based on the immunological measurement method.

The immunological measurement method will be described in greater detail. An example is a sandwich immunological measurement method comprising a step of immobilizing the monoclonal antibody (first monoclonal antibody) of the present invention on a solid phase and incubating it with a sample containing antigen; a step of adding a labeled second monoclonal antibody and incubating the mixture obtained; and a step of detecting the labeled antigen-antibody complex that has been produced in the mixture. In the immunological measurement method of the present invention, the sample, immobilized first monoclonal antibody, and labeled second monoclonal antibody can be simultaneously incubated. Any sandwich immunological measurement method such as the sandwich radioimmunoassay (RIA), sandwich enzymatic immunoassay (EIA), sandwich fluorescent immunoassay (FIA), sandwich luminescence immunoassay method (CLIA), sandwich luminescence enzymatic immunoassay (CLEIA), and sandwich assay-based immunochromatography can be applied as the sandwich immunological measurement method depending on the detection method. The RIA and EIA methods are desirable for quantification.

The sandwich RIA method can be conducted based on a desirable embodiment. In the sandwich RIA method, specifically, beads on which a first monoclonal antibody (the monoclonal antibody of the present invention) has been immobilized are admixed to a standard solution or sample and the mixture is incubated for from 1 to 4 hours, desirably 2 hours, at from 4 to 45° C., desirably 25 to 37° C. (first reaction). After cleaning, a solution containing a second monoclonal antibody that has been labeled with $^{125}I$ for example is added and the mixture is incubated for from 1 to 4 hours, desirably 2 hours, at from 4 to 45° C., desirably 25 to 37° C. (second reaction). Following cleaning, the radioactivity of the antigen-antibody complex that has bound to the beads is detected with a gamma counter or the like to measure a quantity. In another desirable implementation mode, the sandwich EIA method is conducted. In the sandwich EIA method, specifically, beads on which a first monoclonal antibody has been immobilized are admixed with a labeled solution or sample, and the mixture is incubated for from 1 to 4 hours, desirably 2 hours, at from 4 to 45° C., desirably 25 to 37° C. (first reaction). Following cleaning, a solution containing a second monoclonal antibody labeled with an enzyme label such as horse radish peroxidase (HRP) is added and the mixture is incubated for from 1 to 4 hours, desirably 2 hours, at from 4 to 45° C., desirably 25 to 37° C. (first reaction) and an immune complex comprised of antibody-antibody is formed on the beads (second reaction). The enzymatic activity on the beads is measured with a substrate specific to the enzyme and, for example, when the enzyme label is HRP, measured by the colorimetric method by means of tetramethylbenzidine (TMB). The quantity captured on the beads can thus be measured. Colorimetric quantification can be conducted with the usual spectrophotometer.

2-3. Detection of Human MUC1

The method of the present invention can be used to detect whether a malignant tumor exhibiting abnormal expression of MUC1 is present in a body fluid sample. By way of example, the malignant tumor exhibiting abnormal expression of MUC1 is selected from the group consisting of breast cancer, prostate cancer, hepatocellular carcinoma, pancreatic cancer, colon cancer, and ovarian cancer. The antibody of the present invention reacts specifically to MUC1, and thus effectively detects malignant tumors such as breast cancer, prostate cancer, hepatocellular carcinoma, pancreatic cancer, colon cancer, and ovarian cancer associated with human MUC1.

The overexpression of MUC1 has been reported in malignant tumors such as breast cancer, prostate cancer, hepatocellular carcinoma, pancreatic cancer, colon cancer, and ovarian cancer. In particular, 90% and higher overexpression of MUC1 has been found in breast cancer, ovarian cancer, and pancreatic cancer. The overexpression of MUC1 accompanies poor prognoses of various cancers. The concentration of free MUC1 in the patient's blood rises (Nonpatent Reference 1).

The occurrence of dramatic change in the O-glucan of MUC1 has been reported to accompany cancerization, cancer progression, and metastatis (Nonpatent Reference 1). In healthy epithelial tissue, O-sugar chain modification in the VNTR region of MUC1 normally consists of polylactosamine long-chain and branched-chain sugars contain 8 to 10 monosaccharide units. Since the extracellular region of normal MUC1 is modified by such large numbers of sugar chains, it exhibits a protecting, hydrating, and lubricating effect on mucosa; a protecting effect from attacks by bacteria and foreign matter; and a regulating effect between cells and on cell matrix interaction. Further, MUC1 is expressed at the cell apex in healthy cells. However, apical expression disappears in cancer cells, becoming nonpolar expression, with MUC1 appearing over the entire cell surface. When that happens, the pattern of O-sugar chain modification in the VNTR region changes drastically, with O-sugar chain modification by simple short sugar chains appearing instead of the complex sugar chains comprised of the long chains and branched chains seen in normal cells. The low sugar-chain modification and nonpolar expression of MUC1 accompanying the development of cancer is caused by exposure of the normal cryptic peptide epitope and the creation of a new carbohydrate epitope. Accordingly, the antibodies of the present invention, which react specifically with these epitopes of MUC1, are able to distinguish between and recognize healthy and cancerous MUC1, and can be used to detect malignant tumors associated with human MUC1. It also becomes possible to attack just MUC1 that is positive for cancer cells.

The immunological measurement kit of the present invention comprises the above-described anti-MUC1 antibodies. Accordingly, the kit of the present invention can be used to detect human MUC1 that is contained in a sample collected from a specimen suspected of being impeded by or afflicted with disease and thus to rapidly and readily determine the presence of an impediment or disease in the specimen. Reagents for determining disease or impediments that employ such immunological measurement methods are widely known. A person having ordinary skill in the art will be able to readily select suitable components other than antibodies. So long as the immunological measurement kit of the present invention is a technique for implementing an immunological measurement method, it can be used as part of any method.

The present invention also provides a method for diagnosing cancer employing the antibodies of the present invention, a diagnostic agent containing the antibodies of the present invention, and a diagnostic kit containing antibodies. The antibodies that are contained in the method for diagnosing cancer, diagnostic agent, and diagnostic kit of the present invention are the antibodies of the present invention as set forth above. The antibodies of the present invention can be used in these diagnoses of cancer because they specifically bind to the specific cancers set forth above.

The antibodies of the present invention can be used as markers for diagnosing the above malignant tumors and for monitoring the progress of disease in patients. In one implementation mode, cancer in a patient can be diagnosed by comparing and evaluating a biological sample obtained from a patient relative to a cutoff value determined in advance based on the MUC1 level.

Measurement results obtained by (b) above and measurement results obtained by the same steps (a) and (b) for a control sample can be compared and used to detect whether a malignant tumor is present in the body fluid sample that has been measured. The control sample can be a body fluid sample obtained from a healthy person.

To determine whether or not cancer is present, a signal detected from a reporter group binding to and remaining on a solid phase support is generally compared to the signal corresponding to a predetermined cutoff value. In one implementation mode, the cutoff value is the average value of a signal obtained by incubating immobilized antibodies along with a sample from a patient without cancer. Generally, a sample is considered to be positive for cancer when it generates a signal exceeding the predetermined cutoff value by three standard deviations. The cutoff value can be determined for example from a plot of a set of the ratio of false positives (100%—specificity) and the ratio of true positives (that is, sensitivity) corresponding to the respective possible cutoff values of diagnostic test results. The cutoff value that is closest to the upper left edge of the plot (that is, the value containing the greatest region) is the most accurate cutoff value. A sample that produced a signal that was higher than the cutoff value determined by the method of the present invention would then be considered to be positive. Alternatively, the cutoff value could either be shifted along with the plots to the left in the plot to minimize the ratio of false positives, or shifted to the right to minimize the ratio of false negatives. Generally, a sample producing a signal higher than the cutoff value determined by this method would be considered to be positive for cancer.

3. The Pharmaceutical Composition

The pharmaceutical composition of the present invention comprises monoclonal antibodies as an active ingredient, is for preventing and/or treating malignant tumors, and can contain any pharmaceutically acceptable support. The malignant tumor is selected from the group consisting of breast cancer, prostate cancer, hepatocellular carcinoma, pancreatic cancer, colon cancer, and ovarian cancer.

The anti-MUC1 antibodies and antigen-binding fragments thereof of the present invention can be used to prevent and/or treat diseases involving MUC1. Diseases involving MUC1 include malignant tumors such as breast cancer, prostate cancer, hepatocellular carcinoma, pancreatic cancer, colon cancer, and ovarian cancer. In patients with these malignant tumors, abnormality in the expression of MUC1, abnormality in the sugar chain structure of MUC1, and resulting functional abnormalities are recognized. Thus, the anti-MUC1 antibodies of the present invention can prevent and/or treat malignant tumors through the effects of suppressing malignant tumors.

The anti-MUC1 antibody and antigen-binding fragment thereof of the present invention suppress the accelerated cell proliferation, cancer metastasis, and the like that occur due to the abnormal MUC1 expression, abnormal sugar chain structure of MUC1, and resulting functional abnormalities that are observed in breast cancer, prostate cancer, hepatocellular carcinoma, pancreatic cancer, colon cancer, and ovarian cancer, permitting the prevent and/or treatment of cancer.

Recently, the interaction between MUC1 and galectin has been found to be important in the metastasis of breast cancer and colon cancer and the like (Nonpatent Reference 11). In the course of cancer cell invasion and metastasis, the cancer cells leave the initial site, invade the surrounding extracellular matrix and endothelial cells, and penetrate blood and lymph vessels. Ultimately, they attach at secondary sites and proliferate. The transmigration of cancer cells from circulation to metastatic sites includes (i) the stopping of circulating cancer cells and transient weak contact (docking) between cancer cells and blood vessel endothelial cells; (ii) inducing local change and ligand expression with various adhesion receptors (integrin, cadherin, and the like), and subsequently (iii) strong adhesion (locking on) of cancer cells to blood vessel endothelial cells. The interaction of MUC1 and galectin 3 has come to be understood to play an important role in these three processes. Galectins are a general term for proteins that recognize the β-galactoside structure and bind to or crosslink sugar chains. Galectin 3 is one of 15 galectins and is known to be present in endothelial cells and in the cytoplasm and nuclei, on the surface, and in the extracellular matrix and the like of immune cells. It has been demonstrated that the MUC1 of cancer cells binds to galectin 3, that the blood concentration of galectin 3 in patients with metastatic cancers increases relative to healthy controls, that the adhesion of circulating cancer cells to vascular endothelial cells depends on the expression of MUC1 by cancer cells and the presence of extracellular galectin 3 in epithelial cells, that the binding of extracellular galectin 3 to cancer cell MUC1 causes marked local change on the cell surface of MUC1, strengthening the bonds between cancer cells and vascular endothelial cells, and the like. It also shows that the interaction between galectin in the blood and MUC1 is an important basic molecular mechanism in the metastasis of cancer cells into distant organs. Accordingly, were it possible to block the binding of MUC1 and galectin 3, it would conceivably be possible to inhibit all of above metastatic processes (i) to (iii) and suppress metastasis.

In the examples given farther below, the antibodies of the present invention are described as blocking the binding of MUC1 and galectin 3. This suggests that using the antibodies of the present invention, it would be possible to prevent and/or treat the metastasis of cancer that overexpresses MUC1 in the development of cancers such as pancreatic cancer, ovarian cancer, and lung cancer.

The anti-MUC1 monoclonal antibodies of the present invention are mouse antibodies. The antibodies employed in the pharmacological composition of the present invention are desirably mouse antibodies that have been converted into chimeric antibodies, humanized antibodies, or fully human antibodies. Mouse antibodies can be converted into chimeric antibodies, humanized antibodies, or full human antibodies using known methods.

The pharmacological composition of the present invention can be formulated by methods known to persons having ordinary skill in the art with active ingredients in the form of the antibodies of the present invention. For example, it can be used parenterally in the form of a sterile solution in water or some other pharmaceutically acceptable liquid, or as the injection of a suspension. For example, formulation is conceivable by suitable combination with a pharmaceutically acceptable support or medium, specifically, sterile water, physiological saline, a vegetable oil, an emulsifier, a suspension agent, a surfactant, a stabilizer, a flavoring agent, an excipient, a vehicle, a preservative, a binder, or the like and mixing in the unit dose form required by generally recognized formulations. The quantity of the active ingredient in these formulations is determined so as to yield a suitable dose within the indicated range.

A sterile composition for injection can be formulated according to the usual formulations employing a vehicle such as injection-use distilled water. Examples of injection-use aqueous solutions are physiological saline and isotonic solutions containing glucose or some other adjuvant, such as D-sorbitol, D-mannose, D-mannitol, sodium chloride. For example, suitable solubilizing agents such as alcohols, specifically, ethanol and polyalcohols such as propylene glycol and polyethylene glycol, and nonionic surfactants such as polysorbate 80™ and HCO-6, can be used in combination.

Examples of oily liquids are sesame oil and soybean oil; solubilizing agents in the form of benzyl benzoate and benzyl alcohol can be employed in combination. Buffers such as phosphate buffers, sodium acetate buffers; soothing agents such as procaine hydrochloride; stabilizers such as benzyl alcohol and phenol; and oxidation inhibitors can also be formulated. The injection that is prepared is normally loaded into a suitable ampule. For delivery to cells, liposomes can be used to encapsulate the drug.

Administration can be oral or parenteral. Parenteral administration is desirable. Specific examples are injections, nasally administered agents, agents administered through the lungs, and transdermal administration. Examples are systematic or local administration in the form of an injection such as an intravenous injection, intramuscular injection, intraperitoneal injection, or subcutaneous injection.

The dose and administration method of the antibodies of the present invention can be suitably selected based on the patient's age, weight, and sex; the nature of the symptoms being treated; their severity; and the like. By way of example, a single dose of the pharmaceutical composition containing the antibodies can be selected within a range of from 0.0001 mg to 1,000 mg per kg of body weight. Alternatively, the dosage administered can be selected from within a range of from 0.01 to 100,000 mg/body of the patient. However, these numbers are not necessarily limits. The dose administered and the method of administration can be suitably varied based on the patient's age, weight, sex, symptoms, and the like. A person having ordinary skill in the art will be able to make a suitable selection.

EXAMPLES

The present invention will be described in greater detail below through examples. However, the present invention is not limited to these examples.

Glycopeptide Synthesis

The method of synthesizing glycopeptides for evaluating the specificity of the antibodies is given below. A compound with a sequence linked to a crosslinking ketone for use in specificity evaluation, and Cys in Compounds 1 to 4, was synthesized for each compound.

Synthesis of 5-Oxohexanoyl-Gly-Val-Thr-Ser-Ala-Pro-Asp-Thr-Arg-Pro-Ala-Pro-Gly-Ser-Thr-Ala-Pro-Pro-Ala-His-Gly-Val-Thr-Cys-NH$_2$ (Compound 1)

A peptide solid phase was synthesized using a solid phase support in the form of TentaGel S RAM resin (0.24 mmol/g, 50 mg, 12 µmol). The amino acid extension reaction was conducted under conditions of microwave irradiation (40 W, 2,450 MHz, 50° C.) by reacting Fmoc amino acid derivative (48 µmol), HBTU (48 µmol), HOBt (48 µmol) and DIEA (72 µmol) in a DMF solution for six minutes. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was purified by reverse-phase high-performance liquid chromatography, yielding Compound 1 in the form of a freeze-dried powder (6.3 mg, yield 22%).

Synthesis of 5-Oxohexanoyl-Gly-Val-Thr-Ser-Ala-Pro-Asp-Thr(Tn)-Arg-Pro-Ala-Pro-Gly-Ser-Thr-Ala-Pro-Pro-Ala-His-Gly-Val-Thr-Cys-NH$_2$ (Compound 2)

A glycopeptide solid phase was synthesized using a solid phase support in the form of TentaGel S RAM resin (0.24 mmol/g, 100 mg, 36 µmol). The amino acid extension reaction was conducted under conditions of microwave irradiation (40 W, 2,450 MHz, 50° C.) by reacting Fmoc amino acid derivative (144 µmol), HBTU (144 µmol), HOBt (144 µmol) and DIEA (216 µmol) in a DMF solution for six minutes. The sugar chain substitution amino acid extension reaction was conducted by reacting Fmoc-Thr(Ac$_3$GalNacα (1→O)) (43 µmol), HBTU (43 µmol), and HOBt (43 µmol) and DIEA (108 µmol) in a DMF solution for 10 minutes with microwave irradiation. HBTU (43 µmol) and HOBt (43 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 2 in the form of a freeze-dried powder (13.3 mg, yield 15%).

Synthesis of 5-Oxohexanoyl-Gly-Val-Thr-Ser-Ala-Pro-Asp-Thr(T)-Arg-Pro-Ala-Pro-Gly-Ser-Thr-Ala-Pro-Pro-Ala-His-Gly-Val-Thr-Cys-NH$_2$ (Compound 3)

A glycopeptide solid phase was synthesized using a solid phase support in the form of TentaGel S RAM resin (0.24 mmol/g, 200 mg, 48 µmol). The amino acid extension reaction was conducted under conditions of microwave irradiation (40 W, 2,450 MHz, 50° C.) by reacting Fmoc amino acid derivative (192 µmol), HBTU (192 µmol), HOBt (192 µmol) and DIEA (288 µmol) in a DMF solution for six minutes. The sugar chain substitution amino acid extension reaction was conducted by reacting Fmoc-Thr(Ac$_4$Galβ (1→3)Ac$_2$GalNAcα(1→O) (58 µmol), HBTU (58 µmol), and HOBt (58 µmol) and DIEA (144 µmol) in a DMF solution for 10 minutes with microwave irradiation. HBTU (58 µmol) and HOBt (58 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 3 in the form of a freeze-dried powder (22.0 mg, yield 17%).

Synthesis of 5-Oxohexanoyl-Gly-Val-Thr-Ser-Ala-Pro-Asp-Thr(Sialyl-T)-Arg-Pro-Ala-Pro-Gly-Ser-Thr-Ala-Pro-Pro-Ala-His-Gly-Val-Thr-Cys-NH$_2$ (Compound 4)

Compound 3 (10 mM, 300 µL, water) was mixed with a reaction solution obtained by mixing 1,000 mM HEPES buffer (pH 7.3, 30 µL), 1,000 mM HEPES buffer (pH 7.0, 30 µL), 1,000 mM MnCl$_2$ (6 µL), 150 mM CMP-NeuAc (60 µL), 1.4 U/mL α2,3-(O)-Sialyltransferase, Rat, Recombinant, S. frugiperda (30 µL, Calbiochem), and water (74 µL). The mixture was incubated for 24 hours at 25° C., after which the reaction liquid was purified by reverse-phase high-performance liquid chromatography, yielding Compound 4 in the form of a freeze-dried powder (5.5 mg, 60% yield).

Synthesis of 5-Oxohexanoyl-Gly-Val-Thr-Ser-Ala-Pro-Asp-Thr-Arg-Pro-Ala-Pro-Gly-Ser-Thr-Ala-Pro-Pro-Ala-His-Gly-Val-Thr-NH$_2$ (Compound 5)

A peptide solid phase was synthesized using a solid phase support in the form of Rink Amide-ChemMatrix resin (0.45 mmol/g, 100 mg, 45 µmol, a product of Biotage). The amino acid extension reaction was conducted under conditions of microwave irradiation (40 W, 2,450 MHz, 50° C.) by reacting Fmoc amino acid derivative (180 µmol), HBTU (180 µmol), HOBt (180 µmol) and DIEA (270 µmol) in a DMF solution for 6 minutes. The mixture was treated for 1 minute at room temperature with an acetic anhydride/DIEA/

DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hour with trifluoroacetic acid:water (95:2.5, v/v). The reaction solution was filtered, ether was added to induce precipitation, and coarse crystals were obtained. The coarse product was purified by reverse-phase high-performance liquid chromatography, yielding Compound 5 in the form of a freeze-dried powder (45.8 mg, yield 45%).

Synthesis of 5-Oxohexanoyl-Gly-Val-Thr-Ser-Ala-Pro-Asp-Thr(Tn)-Arg-Pro-Ala-Pro-Gly-Ser-Thr-Ala-Pro-Pro-Ala-His-Gly-Val-Thr-NH$_2$ (Compound 6)

A glycopeptide solid phase was synthesized using a solid phase support in the form of Rink Amide-ChemMatrix resin (0.45 mmol/g, 100 mg, 45 μmol). The amino acid extension reaction was conducted under conditions of microwave irradiation (40 W, 2,450 MHz, 50° C.) by reacting Fmoc amino acid derivative (180 μmol), HBTU (180 μmol), HOBt (180 μmol) and DIEA (270 μmol) in a DMF solution for 6 minutes. The sugar chain substitution amino acid extension reaction was conducted by reacting Fmoc-Thr(Ac$_3$GalNacα (1→O)) (54 μmol), HBTU (54 μmol), and HOBt (54 μmol) and DIEA (135 μmol) in a DMF solution for 10 minutes with microwave irradiation. HBTU (54 μmol) and HOBt (54 μmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:2.5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 6 in the form of a freeze-dried powder (43.2 mg, yield 39%).

Synthesis of 5-Oxohexanoyl-Gly-Val-Thr-Ser-Ala-Pro-Asp-Thr-Ara-Pro-Ala-Pro-Gly-Ser(Tn)-Thr-Ala-Pro-Pro-Ala-His-Gly-Val-Thr-NH$_2$ (Compound 7)

A glycopeptide solid phase was synthesized using a solid phase support in the form of Rink Amide-ChemMatrix resin (0.45 mmol/g, 100 mg, 45 μmol). The amino acid extension reaction was conducted under conditions of microwave irradiation (40 W, 2,450 MHz, 50° C.) by reacting Fmoc amino acid derivative (180 μmol), HBTU (180 μmol), HOBt (180 μmol) and DIEA (270 μmol) in a DMF solution for 6 minutes. The sugar chain substitution amino acid extension reaction was conducted by reacting Fmoc-Ser(Ac$_3$GalNacα (1→O)) (54 μmol), HBTU (54 μmol), and HOBt (54 μmol) and DIEA (135 μmol) in a DMF solution for 10 minutes with microwave irradiation. HBTU (54 μmol) and HOBt (54 μmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:2.5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 7 in the form of a freeze-dried powder (21.1 mg, yield 19%).

Synthesis of 5-Oxohexanoyl-Gly-Val-Thr-Ser-Ala-Pro-Asp-Thr-Arg-Pro-Ala-Pro-Gly-Ser-Thr(Tn)-Ala-Pro-Pro-Ala-His-Gly-Val-Thr-NH$_2$ (Compound 8)

A glycopeptide solid phase was synthesized using a solid phase support in the form of Rink Amide-ChemMatrix resin (0.45 mmol/g, 100 mg, 45 μmol). The amino acid extension reaction was conducted under conditions of microwave irradiation (40 W, 2,450 MHz, 50° C.) by reacting Fmoc amino acid derivative (180 μmol), HBTU (180 μmol), HOBt (180 μmol) and DIEA (270 μmol) in a DMF solution for 6 minutes. The sugar chain substitution amino acid extension reaction was conducted by reacting Fmoc-Thr(Ac$_3$GalNacα (1→O)) (54 μmol), HBTU (54 μmol), and HOBt (54 μmol) and DIEA (135 μmol) in a DMF solution for 10 minutes with microwave irradiation. HBTU (54 μmol) and HOBt (54 μmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:2.5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 8 in the form of a freeze-dried powder (48.2 mg, yield 43%).

Synthesis of 5-Oxohexanoyl-Gly-Val-Thr(Tn)-Ser(Tn)-Ala-Pro-Asp-Thr(Tn)-Arg-Pro-Ala-Pro-Gly-Ser(Tn)-Thr(Tn)-Ala-Pro-Pro-Ala-His-Gly-Val-Thr-NH$_2$ (Compound 9)

A glycopeptide solid phase was synthesized using a solid phase support in the form of Rink Amide-ChemMatrix resin (0.45 mmol/g, 100 mg, 45 μmol). The amino acid extension reaction was conducted under conditions of microwave irradiation (40 W, 2,450 MHz, 50° C.) by reacting Fmoc amino acid derivative (180 µmol), HBTU (180 µmol), HOBt (180 µmol) and DIEA (270 µmol) in a DMF solution for 6 minutes. The sugar chain substitution amino acid extension reaction was conducted by reacting Fmoc-Thr(Ac$_3$GalNacα (1→O)) or Fmoc-Ser(Ac$_3$GalNacα(1→O)) (54 µmol), HBTU (54 µmol), and HOBt (54 µmol) and DIEA (135 µmol) in a DMF solution for 10 minutes with microwave irradiation. HBTU (54 µmol) and HOBt (54 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:2.5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 9 in the form of a freeze-dried powder (37.8 mg, yield 25%).

Synthesis of 5-Oxohexanoyl-Gly-Val-Thr-Ser-Ala-Pro-Asp-Thr(T)-Arg-Pro-Ala-Pro-Gly-Ser-Thr-Ala-Pro-Pro-Ala-His-Gly-Val-Thr-NH$_2$ (Compound 10)

A glycopeptide solid phase was synthesized using a solid phase support in the form of Rink Amide-ChemMatrix resin (0.90 mmol/g, 200 mg, 90 µmol). The amino acid extension reaction was conducted under conditions of microwave irradiation (40 W, 2,450 MHz, 50° C.) by reacting Fmoc amino acid derivative (360 µmol), HBTU (360 µmol), HOBt (360 µmol) and DIEA (540 µmol) in a DMF solution for 6 minutes. The sugar chain substitution amino acid extension reaction was conducted by reacting Fmoc-Thr(Ac$_3$GalNacβ (1→3) Ac$_2$GalNacα(1→O)) (108 µmol), HBTU (108 µmol), and HOBt (108 µmol) and DIEA (270 µmol) in a DMF solution for 10 minutes with microwave irradiation. HBTU (108 µmol) and HOBt (108 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:2.5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 10 in the form of a freeze-dried powder (110 mg, yield 46%).

Synthesis of 5-Oxohexanoyl-Gly-Val-Thr-Ser-Ala-Pro-Asp-Thr(Sialyl-T)-Arg-Pro-Ala-Pro-Gly-Ser-Thr-Ala-Pro-Pro-Ala-His-Gly-Val-Thr-NH$_2$ (Compound 11)

Compound 8 (10 mM, 496 µL, water) was mixed with a reaction solution obtained by mixing 1,000 mM HEPES buffer (pH 7.0, 30 µL), 1,000 mM MnCl$_2$ (8 µL), 200 mM CMP-NeuAc (95 µL), 1.4 U/mL α2,3-(O)-Sialyltransferase, Rat, Recombinant, S. frugiperda (28 µL, Calbiochem), and water (212 µL). The mixture was incubated for 24 hours at 25° C., after which the reaction liquid was purified by reverse-phase high-performance liquid chromatography, yielding Compound 11 in the form of a freeze-dried powder (14 mg, 96% yield).

Synthesis of 5-Oxohexanoyl-Pro-Pro-Thr-Thr-Thr-Pro-Ser-Pro-Pro-Pro-Thr-Ser-Thr-Thr-Leu-Pro-Pro-Thr-NH$_2$ (Compound 12)

A peptide solid phase was synthesized using a solid phase support in the form of Rink Amide-ChemMatrix resin (0.48 mmol/g, 25 mg, 12 µmol). The amino acid extension reaction was conducted under conditions of microwave irradiation (40 W, 2,450 MHz, 50° C.) by reacting Fmoc amino acid derivative (48 µmol), HBTU (48 µmol), HOBt (48 µmol) and DIEA (72 µmol) in a DMF solution for 9 minutes. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 1 hour with trifluoroacetic acid:water:triisopropylsilane (95:2.5:2.5, v/v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 12 in the form of a freeze-dried powder (7.2 mg, yield 30%).

Synthesis of 5-Oxohexanoyl-Pro-Pro-Thr-Thr(Tn)-Thr(Tn)-Pro-Ser-Pro-Pro-Pro-Thr-Ser-Thr-Thr(Tn)-Thr(Tn)-Leu-Pro-Pro-Thr-NH$_2$ (Compound 13)

A glycopeptide solid phase was synthesized using a solid phase support in the form of Rink Amide-ChemMatrix resin (0.48 mmol/g, 25 mg, 12 µmol). The amino acid extension reaction was conducted under conditions of microwave irradiation (40 W, 2,450 MHz, 50° C.) by reacting Fmoc amino acid derivative (48 µmol), HBTU (48 µmol), HOBt (48 µmol) and DIEA (72 µmol) in a DMF solution for 9 minutes. The sugar chain substitution amino acid extension reaction was conducted by reacting Fmoc-Thr(Ac$_3$GalNacα (1→O)) (14 µmol), PyBOP (14 µmol), and HOBt (14 µmol) and DIEA (36 µmol) in a DMF solution for 10 minutes with microwave irradiation. PyBOP (14 µmol) and HOBt (14 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water:triisopropylsilane (95:2.5:2.5, v/v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 13 in the form of a freeze-dried powder (4.7 mg, yield 14%).
Synthesis of 5-Oxohexanoyl-Ser-Ala-Ser-Thr-Gly-His-Ala-Thr-Pro-Leu-Pro-Val-Thr-Asp-Thr-Ser-Cys-NH$_2$ (Compound 14)

A peptide solid phase was synthesized using a solid phase support in the form of TentaGel S RAM resin (0.24 mmol/g, 200 mg, 48 µmol, obtained from Rapp Polymere, GmbH). The amino acid extension reaction was conducted under conditions of microwave irradiation (40 W, 2,450 MHz, 50° C.) by reacting Fmoc amino acid derivative (192 µmol), HBTU (192 µmol), HOBt (192 µmol) and DIEA (288 µmol) in a DMF solution for six minutes. HBTU (58 µmol) and HOBt (58 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was purified by reverse-phase high-performance liquid chromatography, yielding Compound 14 in the form of a freeze-dried powder (9.0 mg, yield 11%).
Synthesis of 5-Oxohexanoyl-Ser-Ala-Ser-Thr-Gly-His-Ala-Thr(Tn)-Pro-Leu-Pro-Val-Thr-Asp-Thr-Ser-Cys-NH$_2$ (Compound 15)

A peptide solid phase was synthesized using a solid phase support in the form of TentaGel S RAM resin (0.24 mmol/g, 200 mg, 48 µmol, obtained from Rapp Polymere, GmbH). The amino acid extension reaction was conducted under conditions of microwave irradiation (40 W, 2,450 MHz, 50° C.) by reacting Fmoc amino acid derivative (192 µmol), HBTU (192 µmol), HOBt (192 µmol) and DIEA (288 µmol) in a DMF solution for six minutes. The mixture was treated for 1 minute at room temperature with an acetic anhydride/DIEA/DMF (10:5:85, v/v/v) solution to acetylate the unreacted amino groups. The sugar chain substitution amino acid extension reaction was conducted by reacting Fmoc-Thr(Ac3GalNacα(1→O)) (58 µmol), HBTU (58 µmol), and HOBt (58 µmol) and DIEA (144 µmol) in a DMF solution for 10 minutes with microwave irradiation. HBTU (58 µmol) and HOBt (58 µmol) were added and the mixture was reacted for 10 minutes with microwave irradiation. The mixture was treated for 1 minute at room temperature with an acetic anhydride/DIEA/DMF (10:5:85, v/v/v) solution to acetylate the unreacted amino groups. Next, with microwave irradiation (40 W, 2,450 MHz, 50° C.), a 20% piperidine/DMF treatment was conducted for 3 minutes to remove the Fmoc group protection. In glycopeptide synthesis, the three steps of (1) extension with various Fmoc amino acids, (2) acetylation treatment, and (3) Fmoc removal were repeatedly sequentially conducted. The solid phase resin obtained was treated for 2 hours with trifluoroacetic acid:water (95:5, v/v). The reaction solution was filtered, ether was added to induce precipitation, and coarse crystals were obtained. The coarse product was dissolved in methanol, 1 N sodium hydroxide aqueous solution was added to adjust the solution to pH 12.0 to 12.5, and processing was conducted for 1 hour at room temperature. To this was added 10% acetic acid to adjust the solution to the vicinity of pH 7, after which the solvent was distilled off. The residue obtained was purified by reverse-phase high-performance liquid chromatography, yielding Compound 15 in the form of a freeze-dried powder (13.0 mg, yield 14%).

Figure 1B:
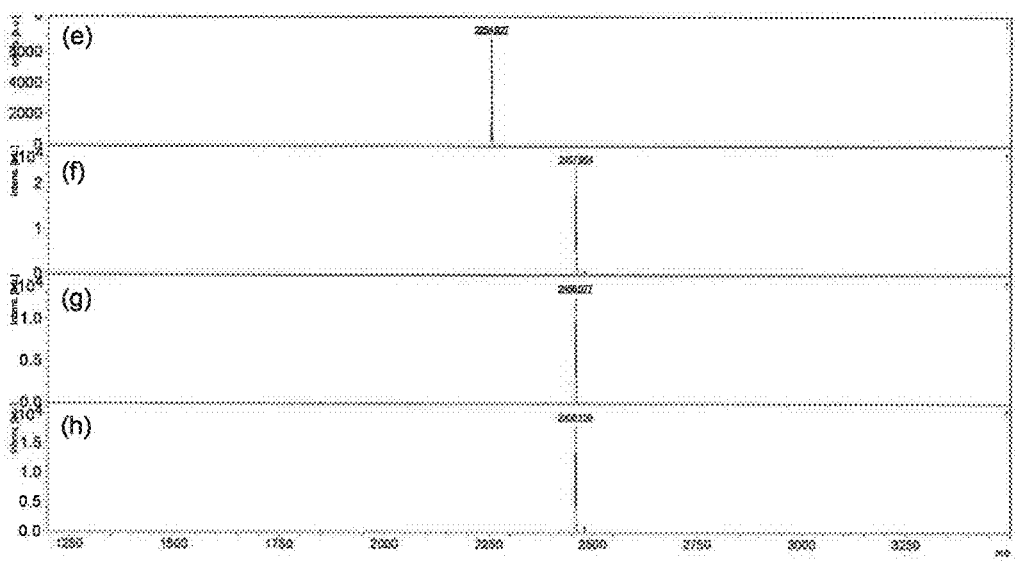
Figure 1C:
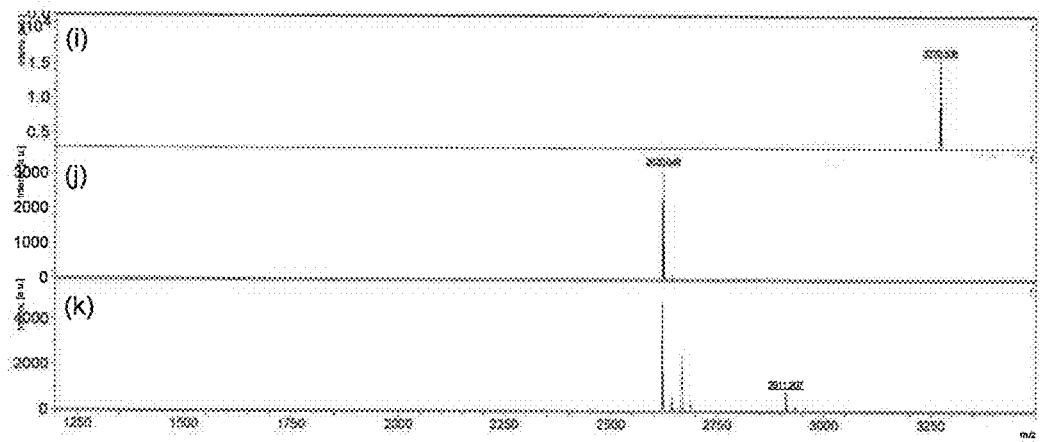
Figure 2:
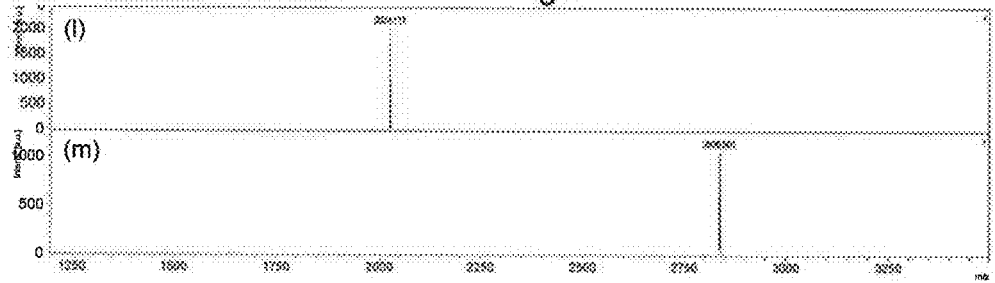
FIG. 2 A MALDI-TOFMS spectrum of MUC2-derived glycopeptides.

Summary of Identification Data of Compounds 1 to 15:
MALDI-TOFMS spectrum of glycopeptide derived from MUC1: FIG. 1
(a) Compound 1, m/z calcd for C100H160N30O34S [M+H]+ 2358.151, found 2358.383;
(b) Compound 2, m/z calcd for C108H173N31O39S [M+H]+ 2561.231, found 2561.457;
(c) Compound 3, m/z calcd for C114H183N31O44S [M+H]+ 2723.283, found 2723.504;
(d) Compound 4, m/z calcd for C125H200N32O52S [M+H]+3014.379, found 3014.640
(e) Compound 5, m/z calcd for C97H156N29O33 [M+H]+ 2255.142, found 2254.927;
(f) Compound 6, m/z calcd for C105H169N30O38 [M+H]+ 2458.221, found 2457.954;
(g) Compound 7, m/z calcd for C105H169N30O38 [M+H]+ 2458.221, found 2458.077;
(h) Compound 8, m/z calcd for C105H169N30O38 [M+H]+ 2458.221, found 2458.159
(i) Compound 9, m/z calcd for C137H221N34O58 [M+H]+ 3270.538, found 3270.308
(j) Compound 10, m/z calcd for C111H179N30O43 [M+H]+ 2620.274, found 2620.049;
(k) Compound 11, m/z calcd for C122H196N31O51 [M+H]+ 2911.369, found 2911.207;

MALDI-TOFMS spectrum of glycopeptide derived from MUC2: FIG. 2
(l) Compound 12, m/z calcd for C$_{90}$H$_{144}$N$_{20}$O$_{31}$ [M+Na]+ 2024.020, found 2024.111;
(m) Compound 13, m/z calcd for C$_{122}$H$_{196}$N$_{24}$O$_{51}$ [M+Na]+ 2836.338, found 2836.501.

Figure 3:
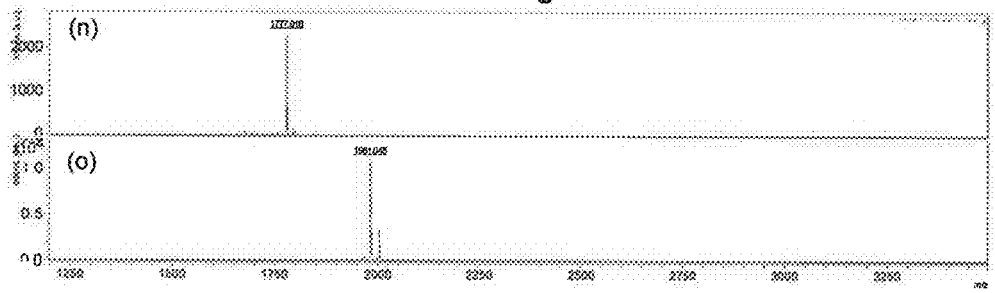
FIG. 3 A MALDI-TOFMS spectrum of MUC4-derived glycopeptides.

MALDI-TOFMS spectrum of glycopeptide derived from MUC4: FIG. 3
(n) Compound 14, m/z calcd for C73H181N20O28S [M+Na]+ 1777.804, found 1777.910;
(o) Compound 15, m/z calcd for C81H131N21O33S [M+Na]+ 1980.884, found 1981.045;

Example 1 Preparation of Monoclonal Antibody Employing Gly-Val-Thr-Ser-Ala-Pro-Asp-Thr(Tn)-Arg-Pro-Ala-Pro-Gly-Ser-Thr-Ala-Pro-Pro-Ala-His-Gly-Val-Thr as Antigen Compound Gly-Val-Thr-Ser-Ala-Pro-Asp-Thr(Tn)-Arg-Pro-Ala-Pro-Gly-Ser-Thr-Ala-Pro-Pro-Ala-His-Gly-Val- Thr Cys-NH$_2$ (85 μg), obtained by adding Cys required for binding carrier protein to C-terminal of Gly-Val-Thr-Ser-Ala-Pro-Asp-Thr(Tn)-Arg-Pro-Ala-Pro-Gly-Ser-Thr-Ala-Pro-Pro-Ala-His-Gly-Val-Thr, was conjugated with keyhole limpet hemocyanin (KLH) and administered to the tail base of BDF (Registered trademark)-1 mice to induce an immune response. The same method was employed 17 hours later to conduct additional immunization with Compound 3. Blood was collected 3 days later and the iliac lymph nodes were collected. The cells collected were fused with myeloma SP2 cells. The hybridomas were cultured in HAT selective medium, and the antibody-producing cells were selected. Next, the hybridoma culture supernatant was seeded onto an ELISA plate and screened in a binding reaction with Compound 2.

Fused cell cloning was conducted by the limiting dilution method. Hybridoma strains 3A9-4B1 (NPMD, Accession No. NITE BP-01845) producing the targeted monoclonal antibodies SN-101, 3C10-E11 producing the targeted monoclonal antibodies SN-102, respectively, were established.

Example 2 Culturing Cell Strains Producing Monoclonal Antibodies (SN-101 and SN-102) and Obtaining Purified Antibodies Culturing method: SN-101 producing hybridoma strain NITE BP-01845 was grown in RPMI-1640 medium containing 10% fetal bovine serum (FBS). A 22 mL quantity of the serum-free medium Panserin H4000 (PAN-Biotech) was added to the 8.1×10$^6$ cells recovered to obtain a suspension. The cells were cultured to acclimate them to the medium. The acclimated cells were grown to about 1.0×10$^8$ in the same medium and subcultured to 5.0×10$^5$/mL. This was then statically cultured for 2 weeks, at which point the culture supernatant was removed by centrifugation. Another hybridoma strain 3C10-E11 was cultured by the same method to obtain a culture supernatant.

Purification method: SN-101 was purified by the method given below from the hybridoma strain NITE BP-01845 that had been cultured. A 200 mL quantity of culture supernatant was passed through a 0.45 μm filter to obtain a purified antibody material. Alternatively, ammonium sulfate was added to the culture supernatant to achieve 50% saturation, and 10,000 g was centrifuged for 20 minutes to collect the precipitate. This was dissolved in 10 mL of PBS, the solution was dialyzed to obtain a purified material, and this was subjected to affinity chromatography employing a HiTrap Protein G HP column (GE Healthcare). A HiTrap Protein G HP column connected after an ÄKTA Explorer 100 (GE Healthcare) was equilibrated with 20 mM sodium phosphate buffer (pH 7.0), and the culture supernatant was added. Unneeded components that had not bound to the column were washed away with the same buffer, after which antibodies were eluted by a small quantity of 0.1 M glycine-HCl buffer (pH 2.5) and neutralized by the addition of a small quantity of 1 M tris-HCl buffer (pH 9.0). The fractions that passed through the column were repeatedly added to the column to increase the collection yield of antibodies. The operations up to this point yielded 2.3 mg of SN-101. From the culture supernatant 200 mL of 3C10-E11, 8.3 mg of SN-102 yielded by the same purification method.

Example 3 Reaction Specificity Evaluation of Antibodies

Preparation of Array of Immobilized Glycopeptide

A substrate for an immobilized sugar chain array (made by Sumitomo Bakelite) was treated for 2 hours at 37° C. with 2 M HCl and the t-butoxycarbonyl group (Boc group) protection was removed. The product was washed twice with water and then dried to place aminoxy groups on the surface of the substrate. A spotting solution (25 mM AcOH/pyridine, 0.005% Triton X-100, pH 5.4) was added to the various synthetic glycopeptides shown in Table 1 to dissolve them. A spotter (BioChip Arrayer, made by Cartesion) employed a spot pin (CMP, pin diameter 0.4 mm, Arraylt Corp.) to spot the substrate. A reaction was conducted for 1 hour at 80° C. to immobilize the glycopeptides on the substrate. Washing was conducted once with water, the product was immersed in 10 mg/mL succinic anhydride, a reaction was conducted for 3 hours at room temperature, and the unreacted aminooxy groups were protected. Washing was conducted twice with water and the product was dried.

Figure 4D:
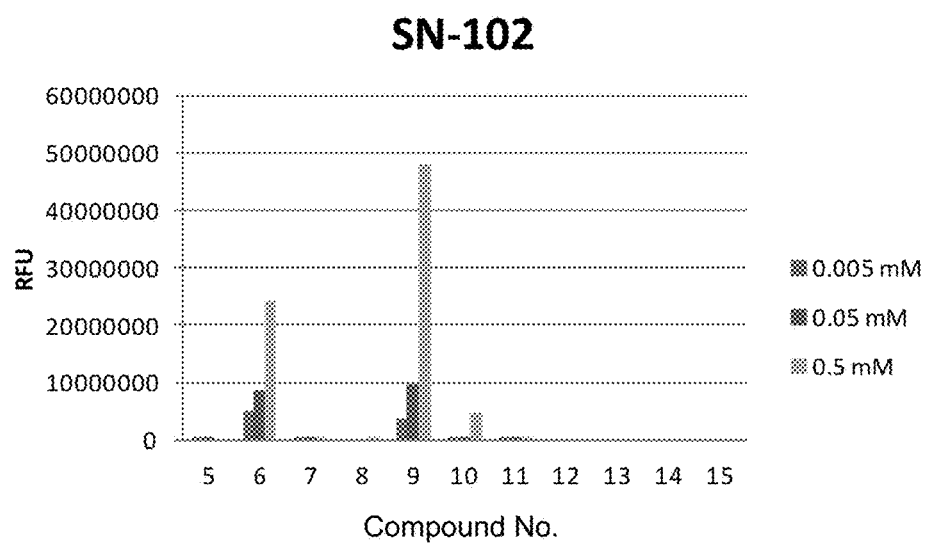

The reaction supernatant was diluted 10-fold with the reaction solution given below. A Hybricover (made by Sumitomo Bakelite) was placed on the immobilized glycopeptide array, 70 μL of the diluted solution was spread out, and a reaction was conducted for 2 hours at room temperature. The Hybricover was removed and the substrate was washed one time each with cleansing solution and water to clean it. The substrate was dried, the Hybricover was positioned, and Anti-IgG(H+L), mouse, goat-poly, and Cy3 (Rockland Immunochemicals) prepared in 1 μg/mL with the following solutions were seeded on the substrate. These were reacted for 1 hour at room temperature. Following the reaction, the product was washed with cleansing solution. Fluorescent intensity of Cy3 was measured with a scanner (Typhoon TRIO+, GE Healthcare). A fluorescent response digital image was created with Array Vision™ software (GE Healthcare). The results are given in FIG. 4.

Reaction solution: 50 mM Tris·HCl (pH 7.4), 100 mM NaCl, 1 mM CaCl$_2$, MnCl$_2$, MgCl$_2$, 0.05% Tween 20

Cleansing solution: 50 mM Tris·HCl (pH 7.4), 100 mM NaCl, 1 mM CaCl$_2$, MnCl$_2$, MgCl$_2$, 0.05% Triton X-100

TABLE 1

Sequence data of MUC1-derived glycopeptide and analogs thereof
(sequences bound to crosslinking ketone and Cys)

| Origin | Compound No. | Amino acid sequence (N→C) |
|---|---|---|
| MUC1 | 1 | 5-oxohexanoyl-Gly-Val-Thr-Ser-Ala-Pro-Asp-Thr-Arg-Pro-Ala-Pro-Gly-Ser-Thr-Ala-Pro-Pro-Ala-His-Gly-Val-Thr-Cys-NH2 |
|  | 2 | 5-oxohexanoyl-Gly-Val-Thr-Ser-Ala-Pro-Asp-Thr(Tn)-Arg-Pro-Ala-Pro-Gly-Ser-Thr-Ala-Pro-Pro-Ala-His-Gly-Val-Thr-Cys-NH2 |

TABLE 1-continued

Sequence data of MUC1-derived glycopeptide and analogs thereof
(sequences bound to crosslinking ketone and Cys)

| Origin | Compound No. | Amino acid sequence (N→C) |
|---|---|---|
| | 3 | 5-oxohexanoyl-Gly-Val-Thr-Ser-Ala-Pro-Asp-Thr(T)-Arg-Pro-Ala-Pro-Gly-Ser-Thr-Ala-Pro-Pro-Ala-His-Gly-Val-Thr-Cys-NH2 |
| | 4 | 5-oxohexanoyl-Gly-Val-Thr-Ser-Ala-Pro-Asp-Thr(Sialyl-T)-Arg-Pro-Ala-Pro-Gly-Ser-Thr-Ala-Pro-Pro-Ala-His-Gly-Val-Thr-Cys-NH2 |
| | 5 | 5-oxohexanoyl-Gly-Val-Thr-Ser-Ala-Pro-Asp-Thr-Arg-Pro-Ala-Pro-Gly-Ser-Thr-Ala-Pro-Pro-Ala-His-Gly-Val-Thr-NH2 |
| | 6 | 5-oxohexanoyl-Gly-Val-Thr-Ser-Ala-Pro-Asp-Thr(Tn)-Arg-Pro-Ala-Pro-Gly-Ser-Thr-Ala-Pro-Pro-Ala-His-Gly-Val-Thr-NH2 |
| | 7 | 5-oxohexanoyl-Gly-Val-Thr-Ser-Ala-Pro-Asp-Thr-Arg-Pro-Ala-Pro-Gly-Ser(Tn)-Thr-Ala-Pro-Pro-Ala-His-Gly-Val-Thr-NH2 |
| | 8 | 5-oxohexanoyl-Gly-Val-Thr-Ser-Ala-Pro-Asp-Thr-Arg-Pro-Ala-Pro-Gly-Ser-Thr(Tn)-Ala-Pro-Pro-Ala-His-Gly-Val-Thr-NH2 |
| | 9 | 5-oxohexanoyl-Gly-Val-Thr(Tn)-Ser(Tn)-Ala-Pro-Asp-Thr(Tn)-Arg-Pro-Ala-Pro-Gly-Ser(Tn)-Thr(Tn)-Ala-Pro-Pro-Ala-His-Gly-Val-Thr-NH2 |
| | 10 | 5-oxohexanoyl-Gly-Val-Thr-Ser-Ala-Pro-Asp-Thr(T)-Arg-Pro-Ala-Pro-Gly-Ser-Thr-Ala-Pro-Pro-Ala-His-Gly-Val-Thr-NH2 |
| | 11 | 5-oxohexanoyl-Gly-Val-Thr-Ser-Ala-Pro-Asp-Thr(Sialyl-T)-Arg-Pro-Ala-Pro-Gly-Ser-Thr-Ala-Pro-Pro-Ala-His-Gly-Val-Thr-NH2 |
| MUC2 | 12 | 5-oxohexanoyl-Pro-Pro-Thr-Thr-Thr-Pro-Ser-Pro-Pro-Thr-Ser-Thr-Thr-Thr-Leu-Pro-Pro-Thr-NH2 |
| | 13 | 5-oxohexanoyl-Pro-Pro-Thr-Thr(Tn)-Thr(Tn)-Pro-Ser-Pro-Pro-Thr-Ser-Thr-Thr(Tn)-Thr(Tn)-Leu-Pro-Pro-Thr-NH2 |
| MUC4 | 14 | 5-oxohexanoyl-Ser-Ala-Ser-Thr-Gly-His-Ala-Thr-Pro-Leu-Pro-Val-Thr-Asp-Thr-Ser-Cys-NH2 |
| | 15 | 5-oxohexanoyl-Ser-Ala-Ser-Thr-Gly-His-Ala-Thr(Tn)-Pro-Leu-Pro-Val-Thr-Asp-Thr-Ser-Cys-NH2 |

Compounds 1 to 4: SEQ ID NO: 3
Compounds 5 to 11: SEQ ID NO: 1
Compounds 12 and 13: SEQ ID NO: 4
Compounds 14 and 15: SEQ ID NO: 5

Characteristics of Antibodies SN-101 and SN-102

Antibodies SN-101 and 102 are respectively recognizes the sugar chain Tn structure and modified positions of MUC1 glycopeptides as below:

SN-101
i) binding to the MUC1-derived glycopeptide Gly-Val-Thr-Ser-Ala-Pro-Asp-(Tn)Thr-Arg-Pro-Ala-Pro-Gly-Ser-Thr-Ala-Pro-Pro-Ala-His-Gly-Val-Thr-Cys;
ii) not binding to a glycopeptide in which the Tn sugar chain of the MUC1-derived glycopeptide has been substituted with T or STn;
iii) not binding to the peptide comprising the amino acid sequence shown by SEQ ID NO: 3 (naked peptide); and
iv) not binding to a glycopeptide in which Tn has been modified in the tandem unit peptide of MUC2 having the amino acid sequence shown by SEQ ID NO: 4 or the tandem unit peptide of MUC4 having the amino acid sequence denoted by SEQ ID NO: 5.

SN-102
i) binding to the glycopeptide Gly-Val-Thr-Ser-Ala-Pro-Asp-(Tn)Thr-Arg-Pro-Ala-Pro-Gly-Ser-Thr-Ala-Pro-Pro-Ala-His-Gly-Val-Thr in which a Tn sugar chain is bonded to the position 8 threonine of the peptide having the amino acid sequence shown in SEQ ID NO: 1;
ii) not binding to, or binding only weakly to, glycopeptides in which the Tn sugar chain of the MUC1-derived glycopeptide has been substituted with T or STn;
iii) not binding to the peptide comprising the amino acid sequence shown by SEQ ID NO: 1 (naked peptide);
iv) not binding to a glycopeptide in which Tn has been modified at the position 14 serine or position 15 threonine in the peptide having the amino acid sequence shown by SEQ ID NO: 1;
v) binding to a glycopeptide in which the Tn sugar chain has been modified at all of the threonines and serines of the peptide having the amino acid sequence shown by SEQ ID NO: 1; and
iv) not binding to a glycopeptide in which Tn has been modified in the tandem unit peptide of MUC2 or the tandem unit peptide of MUC4.

Example 4 Detection of MUC1 Glycopeptides in Patient Serum

An examination was conducted into whether the antigen peptides would be detected in breast cancer, prostate cancer, hepatocellular carcinoma, pancreatic cancer, colon cancer, and ovarian cancer specimen serum using antibody SN-101. The number of specimens was 5 to 10 serum samples from patients who had been clearly clinically diagnosed with the disease and several normal serum samples as negative controls. No antigen glycopeptides were detected in the normal serum but antigen glycopeptides were detected in the patient serum samples.

Example 5 Immunofluorescence Staining of MUC1 Expressing Cells by Antibodies SN-101 and SN-102

Figure 5:
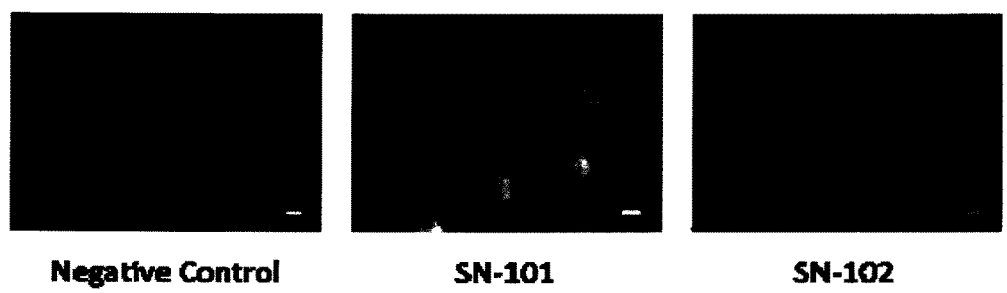
FIG. 5 Results of immunofluorescence staining of MUC1 expression cells with antibody SN-101 or SN-102.

Breast cancer strain OCUB-M was cultured overnight at 37° C. in 5% $CO_2$ in D-MEM containing 10% FBS. The medium was aspirated away. The cell layer was washed with PBS and immobilized for 10 minutes with PBS containing 4% paraformaldehyde. Next, an immersion treatment in PBS containing 0.1% of Triton X™-100 was conducted, followed by 20 minutes of blocking with blocking buffer (1% BSA-containing PBS). A 10 μg/mL solution of antibody SN-101 or SN-102 diluted with blocking buffer was then reacted for 1 hour. A negative control was prepared by reacting blocking solution instead of primary antibody. The antibody solution was removed, washed with PBS, and then reacted with 2 μg/mL Alexa Fluor® 555-labeled anti-mouse IgG antibody. The product was washed with PBS, sealed, and then observed with an all-in-one BZ-9000 (Keyence) fluorescence microscope, yielding a specifically stained image (see FIG. 5).

Example 6 Cell Proliferation-Blocking Test

Figure 6:
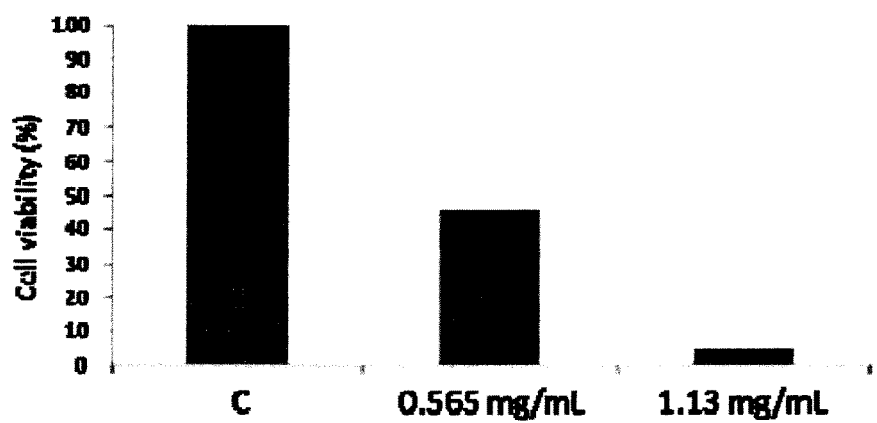
FIG. 6 Results of cell proliferation-blocking test with antibody SN-101.

Breast cancer cells OCUB-M cultured in DMEM (10% FBS) medium were inoculated onto a 96-well plate to $3 \times 10^3$ cells per well. The cells were cultured for 48 hours at 37° C. in a 5% $CO_2$ atmosphere, after which antibody SN-101 was added to a final concentration of 0.565 mg/mL or 1.3 mg/mL. The cells were cultured for 48 hours at 37° C. in a 5% $CO_2$ atmosphere, at which time 20 μL per well of Cell Titer 96 Aqueous One Solution Cell Proliferation Assay (Promega) reagent was added. The cells were then incubated for 2 hours at 37° C. in a 5% $CO_2$ atmosphere. Measurement at an absorbance of 490 nm revealed that the number of cells had decreased in a concentration-dependent manner relative to the control (see FIG. 6).

Example 7 Test of Blocking the Binding of Galectin 3

To each well of an 8-well chamber slide were added $4.8 \times 10^3$ breast cancer cells MCF-7 suspended in RPMI-1640 (10% FBS) and the cells were cultured for 16 hours at 37° C. in a 5% $CO_2$ atmosphere. The medium was aspirated off and 4% formaldehyde in PBS was added to immerse the cells in about 2 mm. The cells were immobilized for 15 minutes. The immobilization solution was aspirated off, and the wells were washed three times with PBS, five minutes each time. Blocking was conducted for 1 hour with blocking buffer (PBS containing 5% BSA). The blocking solution was aspirated off. The antibody alone and mixtures of various concentrations of the antibody and galectin 3 were prepared. These were incubated for 2 hours at 4° C. The antibodies were aspirated off, after which the wells were washed three times with PBS, five minutes each time. Cy5 labeled anti-mouse IgG antibody was added and the mixtures were incubated for 1 hour at room temperature in a dark room. The secondary antibodies were aspirated off, after which the wells were washed three times with PBS, five minutes each time. Observation with a BZ-9000 (KEYENCE) all-in-one fluorescence microscope revealed blocking of the binding of galectin 3 and MUC1 dependent on the antibody concentration.

INDUSTRIAL APPLICABILITY

The present invention provides an antibody that recognizes, with extremely high specificity, glycopeptides in which the tandem unit peptides of human MUC1 have been modified with the O-bond-type sugar chain Tn. Use of the anti-MUC antibody of the present invention permits detection of the presence of MUC1 with high sensitivity, reliably, and conveniently in a manner specific to the epitope of glycopeptides modified with Tn and permits the determination of malignant tumors as illnesses associated with MUC1, and is thus thought to be useful in the field of medical diagnosis. The anti-MUC1 antibody of the present invention also affects the functioning of cancer cells relating to MUC1, and is thus thought to be useful in the field of cancer treatment drugs and the like.

SEQUENCE LISTING FREE TEXT

SEQ ID NO: 1: amino acid sequence of tandem unit peptide of human MUC1
SEQ ID NO: 2: amino acid sequence of tandem unit peptide mutant of human MUC1
SEQ ID NO: 3: amino acid sequence of tandem unit peptide of human MUC1 with cys added to at C-terminal
SEQ ID NO: 4: amino acid sequence of tandem unit peptide of human MUC2
SEQ ID NO: 5: amino acid sequence of tandem unit peptide of human MUC4
SEQ ID NO: 6: amino acid sequence of SN101H
SEQ ID NO: 7: amino acid sequence of SN101L
SEQ ID NO: 8: amino acid sequence of CDR1 of SN101H
SEQ ID NO: 9: amino acid sequence of CDR2 of SN101H
SEQ ID NO: 10: amino acid sequence of CDR3 of SN101H
SEQ ID NO: 11: amino acid sequence of CDR1 of SN101L
SEQ ID NO: 12: amino acid sequence of CDR2 of SN101L
SEQ ID NO: 13: amino acid sequence of CDR3 of SN101L
SEQ ID NO: 14: amino acid sequence of SN1021H
SEQ ID NO: 15: amino acid sequence of SN102L
SEQ ID NO: 16: amino acid sequence of CDR1 of SN102H
SEQ ID NO: 17: amino acid sequence of CDR2 of SN102H
SEQ ID NO: 18: amino acid sequence of CDR3 of SN102H
SEQ ID NO: 19: amino acid sequence of CDR1 of SN102L
SEQ ID NO: 20: amino acid sequence of CDR2 of SN102L
SEQ ID NO: 21: amino acid sequence of CDR3 of SN102L

The invention claimed is:

1. A monoclonal antibody to human MUC1, specifically recognizing human MUC1 tandem units and glycopeptides having a O-bond-type sugar chain core 0 (Tn) on any of the threonines or the serines in the amino acid sequence of the human MUC1 tandem units, wherein said antibody comprises at least one antigen-binding portion comprising an immunoglobulin heavy chain variable region (VH) domain and an immunoglobulin light chain variable region (VL) domain, with the heavy chain variable region domain comprising in the sequence thereof complementarity determining regions CDR1, CDR2, and CDR3, with CDR1 being comprised of the amino acid sequence shown by SEQ ID NO: 8, CDR2 being comprised of the amino acid sequence of SEQ ID NO: 9, and CDR3 being comprised of the amino acid sequence shown by SEQ ID NO: 10, with the light chain variable region domain comprising in the sequence thereof complementarity determining regions CDR1', CDR2', and CDR3', with CDR1' being comprised of the amino acid sequence shown by SEQ ID NO: 11, CDR2' being comprised of the amino acid sequence of SEQ ID NO: 12, and CDR3' being comprised of the amino acid sequence shown by SEQ ID NO: 13; or wherein said antibody comprises at least one antigen-binding portion comprising an immunoglobulin heavy chain variable region (VH) domain and an immunoglobulin light chain variable region (VL) domain, with the heavy chain variable region domain comprising in the sequence thereof complementarity determining regions CDR1, CDR2, and CDR3, with CDR1 being comprised of the amino acid sequence shown by SEQ ID NO: 16, CDR2 being comprised of the amino acid sequence of SEQ ID NO: 17, and CDR3 being comprised of the amino acid sequence shown by SEQ ID NO: 18, with the light chain variable region domain comprising in the sequence thereof complementarity determining regions CDR1', CDR2', and CDR3', with CDR1' being comprised of the amino acid sequence shown by SEQ ID NO: 19, CDR2' being comprised of the amino acid sequence of SEQ ID NO: 20, and CDR3' being comprised of the amino acid sequence shown by SEQ ID NO: 21.

2. The monoclonal antibody according to claim 1, wherein the amino acid sequence of the human MUC1 tandem unit comprises the amino acid sequence shown by SEQ ID NO: 1, and the O-bond-type sugar chain core 0 (Tn) binds to the position eight threonine in the amino acid sequence denoted by SEQ ID NO: 1.

3. The monoclonal antibody according to claim 1, wherein the amino acid sequence of the human MUC1 tandem unit comprises the amino acid sequence shown by SEQ ID NO: 2, and the O-bond-type sugar chain core 0 (Tn) binds to the position eight serine in the amino acid sequence denoted by SEQ ID NO: 2.

4. The monoclonal antibody according to claim 2, having the binding characteristics shown by i) to iii) below:
   i) not binding to a glycopeptide in which the O-bond-type sugar chain core 0 (Tn) has been substituted with a O-bond-type sugar chain T or ST, wherein said glycopeptide has the amino acid sequence of SEQ ID NO: 1;
   ii) not binding to the peptide comprising the amino acid sequence shown by SEQ ID NO: 3 (naked peptide); and
   iii) not binding to a glycopeptide in which Tn has been modified in the tandem unit peptide of MUC2 having the amino acid sequence of SEQ ID NO:4 or the tandem unit peptide of MUC4 having the amino acid sequence of SEQ ID NO: 5.

5. The monoclonal antibody or antigen-binding fragment thereof according to claim 2, wherein the monoclonal antibody is the monoclonal antibody SN-101 having the binding characteristics given by i) to iv) below or being secreted by the hybridoma cell system deposited as Accession Number NITE BP-01845:
   i) binding to the MUC1-derived glycopeptide Gly-Val-Thr-Ser-Ala-Pro-Asp-(Tn)Thr-Arg-Pro-Ala-Pro-Gly-Ser-Thr-Ala-Pro-Pro-Ala-His-Gly-Val-Thr-Cys;
   ii) not binding to a glycopeptide in which the Tn sugar chain of the MUC1-derived glycopeptide has been substituted with T or ST;
   iii) not binding to the peptide comprising the amino acid sequence shown by SEQ ID NO: 3 (naked peptide); and
   iv) not binding to a glycopeptide in which Tn has been modified in the tandem unit peptide of MUC2 having the amino acid sequence of SEQ ID NO: 4 or the tandem unit peptide of MUC4 having the amino acid sequence denoted by SEQ ID NO: 5.

6. The monoclonal antibody or antigen-binding fragment thereof according to claim 2, wherein the monoclonal antibody is the monoclonal antibody SN-102 having the binding characteristics given by i) to vi) below:
   i) binding to the glycopeptide Gly-Val-Thr-Ser-Ala-Pro-Asp-(Tn)Thr-Arg-Pro-Ala-Pro-Gly-Ser-Thr-Ala-Pro-Pro-Ala-His-Gly-Val-Thr in which a Tn sugar chain is bonded to the position 8 threonine of the peptide having the amino acid sequence shown in SEQ ID NO: 1;
   ii) not binding to, or binding only weakly to, glycopeptides in which the Tn sugar chain of the MUC1-derived glycopeptide has been substituted with T or ST, wherein said glycopeptide has the amino acid sequence of SEQ ID NO: 1;
   iii) not binding to the peptide comprising the amino acid sequence shown by SEQ ID NO: 1 (naked peptide);
   iv) not binding to a glycopeptide in which Tn has been modified at the position 14 serine or position 15 threonine in the peptide having the amino acid sequence shown by SEQ ID NO: 1;
   v) binding to a glycopeptide in which the Tn sugar chain has been modified at all of the threonines and serines of the peptide having the amino acid sequence shown by SEQ ID NO: 1; and
   vi) not binding to a glycopeptide in which Tn has been modified in the tandem unit peptide of MUC2 having the amino acid sequence of SEQ ID NO: 4 or the tandem unit peptide of MUC4 having the amino acid sequence of SEQ ID NO: 5.

7. The monoclonal antibody according to claim 1, comprising a heavy chain variable region comprised of the amino acid sequence of SEQ ID NO: 6 and a light chain variable region comprised of the amino acid sequence of SEQ ID NO: 7.

8. The monoclonal antibody thereof according to claim 1, comprising a heavy chain variable region comprised of the amino acid sequence of SEQ ID NO: 14 and a light chain variable region comprised of the amino acid sequence of SEQ ID NO: 15.

9. The monoclonal antibody according to claim 8, for use in specific detection of MUC1.

10. A method for specifically detecting MUC1 in a human body fluid sample, comprising:
   (a) placing the sample in contact with the monoclonal antibody of claim 8; and
   (b) measuring the formation of antibody-antigen complex in the sample following contact.

11. The method according to claim 10, for use in determination of presence of a malignant tumor that exhibits abnormal expression of MUC1 in the body fluid sample.

12. The method according to claim 11, wherein the malignant tumor is selected from the group consisting of breast cancer, prostate cancer, hepatocellular carcinoma, pancreatic cancer, colon cancer, and ovarian cancer.

13. A kit for employing the method described in claim 10, comprising:
   (a) the monoclonal antibody according to any one of claims 1 to 8; and
   (b) a reagent for measuring the antibody-antigen complex.

14. A pharmaceutical composition for treating malignant tumors, comprising an active component in the form of the monoclonal antibody according to claim 8.

15. The composition according to claim 14, wherein the malignant tumor is selected from the group consisting of breast cancer, prostate cancer, hepatocellular carcinoma, pancreatic cancer, colon cancer, and ovarian cancer.

16. The monoclonal antibody according to claim 3, having the binding characteristics shown by i) to iii) below:
   i) not binding to a glycopeptide in which the O-bond-type sugar chain core 0 (Tn) has been substituted with a O-bond-type sugar chain T or ST;
   ii) not binding to the peptide comprising the amino acid sequence shown by SEQ ID NO: 3 (naked peptide); and
   iii) not binding to a glycopeptide in which Tn has been modified in the tandem unit peptide of MUC2 or the tandem unit peptide of MUC4.

17. A pharmaceutical composition for treating malignant tumors, comprising an active component in the form of the monoclonal antibody according to claim 2.

18. A pharmaceutical composition for treating malignant tumors, comprising an active component in the form of the monoclonal antibody according to claim 3.

\* \* \* \* \*

SEQUENCE LISTING

```
<160> NUMBER OF SEQ ID NOS: 33

<210> SEQ ID NO 1
<211> LENGTH: 23
<212> TYPE: PRT
<213> ORGANISM: Homo sapiens
```

```
<400> SEQUENCE: 1

Gly Val Thr Ser Ala Pro Asp Thr Arg Pro Ala Pro Gly Ser Thr Ala
1               5                   10                  15

Pro Pro Ala His Gly Val Thr
            20

<210> SEQ ID NO 2
<211> LENGTH: 23
<212> TYPE: PRT
<213> ORGANISM: Homo sapiens

<400> SEQUENCE: 2

Gly Val Thr Ser Ala Pro Glu Ser Arg Pro Ala Pro Gly Ser Thr Ala
1               5                   10                  15

Pro Pro Ala His Gly Val Thr
            20

<210> SEQ ID NO 3
<211> LENGTH: 24
<212> TYPE: PRT
<213> ORGANISM: Homo sapiens

<400> SEQUENCE: 3

Gly Val Thr Ser Ala Pro Asp Thr Arg Pro Ala Pro Gly Ser Thr Ala
1               5                   10                  15

Pro Pro Ala His Gly Val Thr Cys
            20

<210> SEQ ID NO 4
<211> LENGTH: 19
<212> TYPE: PRT
<213> ORGANISM: Homo sapiens

<400> SEQUENCE: 4

Pro Pro Thr Thr Thr Pro Ser Pro Pro Pro Thr Ser Thr Thr Thr Leu
1               5                   10                  15

Pro Pro Thr

<210> SEQ ID NO 5
<211> LENGTH: 17
<212> TYPE: PRT
<213> ORGANISM: Homo sapiens

<400> SEQUENCE: 5

Ser Ala Ser Thr Gly His Ala Thr Pro Leu Pro Val Thr Asp Thr Ser
1               5                   10                  15

Cys

<210> SEQ ID NO 6
<211> LENGTH: 135
<212> TYPE: PRT
<213> ORGANISM: Homo sapiens

<400> SEQUENCE: 6

Met Asp Leu Arg Leu Ser Cys Ala Phe Ile Ile Val Leu Leu Lys Gly
1               5                   10                  15

Val Gln Ser Glu Val Asn Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45
```

```
Ser Asn Tyr Trp Met Asn Trp Val Arg Gln Ser Pro Glu Lys Gly Leu
    50                  55                  60

Glu Trp Val Ala Gln Ile Arg Leu Lys Ser Asp Asn Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
                100                 105                 110

Gly Ile Tyr Tyr Cys Thr Gly Val Phe Asp Tyr Trp Gly Gln Gly
            115                 120                 125

Thr Thr Leu Thr Val Ser Ser
    130                 135

<210> SEQ ID NO 7
<211> LENGTH: 132
<212> TYPE: PRT
<213> ORGANISM: Homo sapiens

<400> SEQUENCE: 7

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
                20                  25                  30

Ser Leu Gly Asp Gln Ala Ser Ile Ser Cys Arg Ser Ser Gln Ser Leu
            35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
                100                 105                 110

Ser Gln Ser Thr His Val Pro Pro Trp Thr Phe Gly Gly Gly Thr Lys
            115                 120                 125

Leu Glu Ile Lys
    130

<210> SEQ ID NO 8
<211> LENGTH: 5
<212> TYPE: PRT
<213> ORGANISM: Homo sapiens

<400> SEQUENCE: 8

Asn Tyr Trp Met Asn
1               5

<210> SEQ ID NO 9
<211> LENGTH: 19
<212> TYPE: PRT
<213> ORGANISM: Homo sapiens

<400> SEQUENCE: 9

Gln Ile Arg Leu Lys Ser Asp Asn Tyr Ala Thr His Tyr Ala Glu Ser
1               5                   10                  15

Val Lys Gly
```

```
<210> SEQ ID NO 10
<211> LENGTH: 5
<212> TYPE: PRT
<213> ORGANISM: Homo sapiens

<400> SEQUENCE: 10

Gly Val Phe Asp Tyr
1               5

<210> SEQ ID NO 11
<211> LENGTH: 16
<212> TYPE: PRT
<213> ORGANISM: Homo sapiens

<400> SEQUENCE: 11

Arg Ser Ser Gln Ser Leu Val His Ser Asn Gly Asn Thr Tyr Leu His
1               5                   10                  15

<210> SEQ ID NO 12
<211> LENGTH: 7
<212> TYPE: PRT
<213> ORGANISM: Homo sapiens

<400> SEQUENCE: 12

Lys Val Ser Asn Arg Phe Ser
1               5

<210> SEQ ID NO 13
<211> LENGTH: 10
<212> TYPE: PRT
<213> ORGANISM: Homo sapiens

<400> SEQUENCE: 13

Ser Gln Ser Thr His Val Pro Pro Trp Thr
1               5                   10

<210> SEQ ID NO 14
<211> LENGTH: 139
<212> TYPE: PRT
<213> ORGANISM: Homo sapiens

<400> SEQUENCE: 14

Met Lys Cys Ser Trp Ile Ile Phe Phe Leu Met Ala Val Val Thr Gly
1               5                   10                  15

Val Asn Ser Glu Val Gln Leu Gln Gln Ser Gly Ala Glu Leu Val Lys
                20                  25                  30

Pro Gly Ala Ser Val Lys Leu Ser Cys Thr Ala Ser Gly Phe Asn Ile
            35                  40                  45

Lys Asp Tyr Tyr Met His Trp Val Lys Gln Arg Thr Glu Gln Gly Leu
    50                  55                  60

Glu Trp Ile Gly Arg Ile Asp Pro Glu Asp Gly Glu Thr Lys Tyr Ala
65                  70                  75                  80

Pro Lys Phe Gln Gly Lys Ala Ile Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Val His Phe Tyr Tyr Gly Tyr Asp Val Gly Arg Gly Tyr
        115                 120                 125

Trp Gly Gln Gly Thr Thr Leu Thr Val Ser Ser
    130                 135
```

<210> SEQ ID NO 15
<211> LENGTH: 131
<212> TYPE: PRT
<213> ORGANISM: Homo sapiens

<400> SEQUENCE: 15

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Thr Phe Gly Gly Gly Thr Lys Leu
        115                 120                 125

Glu Ile Lys
    130

<210> SEQ ID NO 16
<211> LENGTH: 5
<212> TYPE: PRT
<213> ORGANISM: Homo sapiens

<400> SEQUENCE: 16

Asp Tyr Tyr Met His
1               5

<210> SEQ ID NO 17
<211> LENGTH: 17
<212> TYPE: PRT
<213> ORGANISM: Homo sapiens

<400> SEQUENCE: 17

Arg Ile Asp Pro Glu Asp Gly Glu Thr Lys Tyr Ala Pro Lys Phe Gln
1               5                   10                  15

Gly

<210> SEQ ID NO 18
<211> LENGTH: 11
<212> TYPE: PRT
<213> ORGANISM: Homo sapiens

<400> SEQUENCE: 18

Phe Tyr Tyr Gly Tyr Asp Val Gly Arg Gly Tyr
1               5                   10

<210> SEQ ID NO 19
<211> LENGTH: 17
<212> TYPE: PRT
<213> ORGANISM: Homo sapiens

<400> SEQUENCE: 19

Lys Ser Ser Gln Ser Leu Leu Tyr Ser Ser Asn Gln Lys Asn Tyr Leu
1               5                   10                  15

Ala

<210> SEQ ID NO 20
<211> LENGTH: 7
<212> TYPE: PRT
<213> ORGANISM: Homo sapiens

<400> SEQUENCE: 20

Trp Ala Ser Thr Arg Glu Ser
1               5

<210> SEQ ID NO 21
<211> LENGTH: 7
<212> TYPE: PRT
<213> ORGANISM: Homo sapiens

<400> SEQUENCE: 21

Gln Gln Tyr Tyr Ser Tyr Thr
1               5

<210> SEQ ID NO 22
<211> LENGTH: 116
<212> TYPE: PRT
<213> ORGANISM: Mus musculus

<400> SEQUENCE: 22

Glu Val Asn Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Gln Ile Arg Leu Lys Ser Asp Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Gly Val Phe Asp Tyr Trp Gly Gln Gly Thr Thr Leu
            100                 105                 110

Thr Val Ser Ser
        115

<210> SEQ ID NO 23
<211> LENGTH: 113
<212> TYPE: PRT
<213> ORGANISM: Mus musculus

<400> SEQUENCE: 23

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys

<210> SEQ ID NO 24
<211> LENGTH: 120
<212> TYPE: PRT
<213> ORGANISM: Mus musculus

<400> SEQUENCE: 24

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Thr Glu Gln Gly Leu Glu Trp Ile
        35                  40                  45

Gly Arg Ile Asp Pro Glu Asp Gly Glu Thr Lys Tyr Ala Pro Lys Phe
    50                  55                  60

Gln Gly Lys Ala Ile Ile Thr Ala Asp Thr Ser Asn Thr Ala Tyr
65                  70                  75                  80

Leu Gln Leu Ser Ser Leu Thr Ser Glu Asp Thr Ala Val Tyr Tyr Cys
                85                  90                  95

Val His Phe Tyr Tyr Gly Tyr Asp Val Gly Arg Gly Tyr Trp Gly Gln
            100                 105                 110

Gly Thr Thr Leu Thr Val Ser Ser
        115                 120

<210> SEQ ID NO 25
<211> LENGTH: 111
<212> TYPE: PRT
<213> ORGANISM: Mus musculus

<400> SEQUENCE: 25

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Thr Phe Gly Gly Gly Thr Lys Leu Glu Ile Lys
            100                 105                 110

<210> SEQ ID NO 26
<211> LENGTH: 540
<212> TYPE: DNA
<213> ORGANISM: Mus musculus

<400> SEQUENCE: 26
atggacttga gactgagctg tgctttatt attgttcttt taaaaggggt ccagagtgaa      60

-continued

```
gtgaaccttg aggagtctgg aggaggcttg gtacaacctg gaggatccat gaaactctcc      120
tgtgttgcct ctggattcac tttcagtaac tactggatga actgggtccg ccagtctcca      180 gagaagggc ttgagtgggt tgctcaaatt agattgaaat ctgataatta tgcaacacat       240
tatgcggagt ctgtgaaagg gaggttcacc atctcaagag atgattccaa aagtagtgtc      300
tacctgcaaa tgaacaactt aagggctgaa gacactggaa tttattactg cacaggcggg      360
gtctttgact actggggcca aggcaccact ctcacagtct cctcagccaa aacgacaccc      420
ccatctgtct atccactggc ccctggatct gctgcccaaa ctaactccat ggtgaccctg      480
ggatgcctgg tcaagggcta tttccctgag ccagtgacag tgacctggaa ctctggatcc      540
```

<210> SEQ ID NO 27
<211> LENGTH: 180
<212> TYPE: PRT
<213> ORGANISM: Mus musculus

<400> SEQUENCE: 27

```
Met Asp Leu Arg Leu Ser Cys Ala Phe Ile Ile Val Leu Leu Lys Gly
1               5                   10                  15

Val Gln Ser Glu Val Asn Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Asn Tyr Trp Met Asn Trp Val Arg Gln Ser Pro Glu Lys Gly Leu
    50                  55                  60

Glu Trp Val Ala Gln Ile Arg Leu Lys Ser Asp Asn Tyr Ala Thr His
65                  70                  75                  80

Tyr Ala Glu Ser Val Lys Gly Arg Phe Thr Ile Ser Arg Asp Asp Ser
                85                  90                  95

Lys Ser Ser Val Tyr Leu Gln Met Asn Asn Leu Arg Ala Glu Asp Thr
            100                 105                 110

Gly Ile Tyr Tyr Cys Thr Gly Gly Val Phe Asp Tyr Trp Gly Gln Gly
        115                 120                 125

Thr Thr Leu Thr Val Ser Ser Ala Lys Thr Thr Pro Pro Ser Val Tyr
    130                 135                 140

Pro Leu Ala Pro Gly Ser Ala Ala Gln Thr Asn Ser Met Val Thr Leu
145                 150                 155                 160

Gly Cys Leu Val Lys Gly Tyr Phe Pro Glu Pro Val Thr Val Thr Trp
                165                 170                 175

Asn Ser Gly Ser
            180
```

<210> SEQ ID NO 28
<211> LENGTH: 540
<212> TYPE: DNA
<213> ORGANISM: Mus musculus

<400> SEQUENCE: 28

```
atgaagttgc ctgttaggct gttggtgctg atgttctgga ttcctgcttc cagcagtgat       60
gttgtgatga cccaaactcc actctccctg cctgtcagtc ttggagatca agcctccatc      120
tcttgcagat ctagtcagag ccttgtacac agtaatggaa acacctattt acattggtac      180
ctgcagaagc caggccagtc tccaaagctc ctgatctaca agtttccaa ccgattttct       240 ggggtcccag acaggttcag tggcagtgga tcagggacag atttcacact caagatcagc      300
```

```
agagtggagg ctgaggatct gggagtttat ttctgctctc aaagtacaca tgttcctccg    360
tggacgttcg gtggaggcac caagctggaa atcaaacggg ctgatgctgc accaactgta    420
tccatcttcc caccatccag tgagcagtta acatctggag gtgcctcagt cgtgtgcttc    480
ttgaacaact tctaccccaa agacatcaat gtcaagtgga agattgatgg cagtgaacga    540
```

<210> SEQ ID NO 29
<211> LENGTH: 180
<212> TYPE: PRT
<213> ORGANISM: Mus musculus

<400> SEQUENCE: 29

```
Met Lys Leu Pro Val Arg Leu Leu Val Leu Met Phe Trp Ile Pro Ala
 1               5                  10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Pro Trp Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg
            180
```

<210> SEQ ID NO 30
<211> LENGTH: 726
<212> TYPE: DNA
<213> ORGANISM: Mus musculus

<400> SEQUENCE: 30

```
atgaaatgca gctggatcat cttcttcctg atggcagtgg ttacagggtt caattcagag     60
gttcagctgc agcagtctgg ggcagagctt gtgaagccag gggcctcagt caagttgtcc    120
tgcacagctt ctggcttcaa cattaaagac tactatatgc actgggtgaa gcagaggact    180
gaacagggcc tggagtggat tggaaggatt gatcctgagg atggtgaaac taaatatgcc    240
ccgaaattcc agggcaaggc cattataaca gcagacacat cctccaacac agcctacctg    300
cagctcagca gcctgacatc tgaggacact gccgtctatt actgtgttca cttctactat    360
ggttacgacg taggtcgagg ctactggggc caaggcacca ctctcacagt ctcctcagcc    420
aaaacgacac cccatctgt ctatccactg gcccctggat ctgctgccca aactaactcc    480
atggtgaccc tgggatgcct ggtcaagggc tatttccctg agccagtgac agtgacctgg    540
aactctggat ccctgtccag cggtgtgcac accttcccag ctgtcctgca gtctgacctc    600
```

```
tacactctga gcagctcagt gactgtcccc tccagcacct ggcccagcca gaccgtcacc      660
tgcaacgttg cccacccggc cagcagcacc aaggtggaca gaaaaattgg atccaagggc      720
gaattc                                                                 726
```

<210> SEQ ID NO 31
<211> LENGTH: 242
<212> TYPE: PRT
<213> ORGANISM: Mus musculus

<400> SEQUENCE: 31

```
Met Lys Cys Ser Trp Ile Ile Phe Phe Leu Met Ala Val Val Thr Gly
1               5                   10                  15
Val Asn Ser Glu Val Gln Leu Gln Gln Ser Gly Ala Glu Leu Val Lys
            20                  25                  30
Pro Gly Ala Ser Val Lys Leu Ser Cys Thr Ala Ser Gly Phe Asn Ile
        35                  40                  45
Lys Asp Tyr Tyr Met His Trp Val Lys Gln Arg Thr Glu Gln Gly Leu
    50                  55                  60
Glu Trp Ile Gly Arg Ile Asp Pro Glu Asp Gly Glu Thr Lys Tyr Ala
65                  70                  75                  80
Pro Lys Phe Gln Gly Lys Ala Ile Ile Thr Ala Asp Thr Ser Ser Asn
                85                  90                  95
Thr Ala Tyr Leu Gln Leu Ser Ser Leu Thr Ser Glu Asp Thr Ala Val
            100                 105                 110
Tyr Tyr Cys Val His Phe Tyr Tyr Gly Tyr Asp Val Gly Arg Gly Tyr
        115                 120                 125
Trp Gly Gln Gly Thr Thr Leu Thr Val Ser Ser Ala Lys Thr Thr Pro
    130                 135                 140
Pro Ser Val Tyr Pro Leu Ala Pro Gly Ser Ala Ala Gln Thr Asn Ser
145                 150                 155                 160
Met Val Thr Leu Gly Cys Leu Val Lys Gly Tyr Phe Pro Glu Pro Val
                165                 170                 175
Thr Val Thr Trp Asn Ser Gly Ser Leu Ser Ser Gly Val His Thr Phe
            180                 185                 190
Pro Ala Val Leu Gln Ser Asp Leu Tyr Thr Leu Ser Ser Ser Val Thr
        195                 200                 205
Val Pro Ser Ser Thr Trp Pro Ser Gln Thr Val Thr Cys Asn Val Ala
    210                 215                 220
His Pro Ala Ser Ser Thr Lys Val Asp Lys Lys Ile Gly Ser Lys Gly
225                 230                 235                 240
Glu Phe
```

<210> SEQ ID NO 32
<211> LENGTH: 717
<212> TYPE: DNA
<213> ORGANISM: Mus musculus

<400> SEQUENCE: 32

```
atggattcac aggcccaggt tcttatgtta ctgctgctat gggtatctgg tacctgtggg       60
gacattgtga tgtcacagtc tccatcctcc ctagctgtgt cagttggaga gaaggttact      120
atgagctgca gtccagtca gagccttttta tatagtagca atcaaaagaa ctacttggcc      180
tggtaccagc agaaaccagg gcagtctcct aaactgctga tttactgggc atccactagg      240
gaatctgggg tccctgatcg cttcacaggc agtggatctg ggacagattt cactctcacc      300
```

-continued

```
atcagcagtg tgaaggctga agacctggca gtttattact gtcagcaata ttatagctac    360
acgttcggag gggggaccaa gctggaaata aaacgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata acagctatac ctgtgaggcc    660
actcacaaga catcaacttc acccattgtc aagagcttca acaggaatga gtgttag      717
```

<210> SEQ ID NO 33
<211> LENGTH: 238
<212> TYPE: PRT
<213> ORGANISM: Mus musculus

<400> SEQUENCE: 33

```
Met Asp Ser Gln Ala Gln Val Leu Met Leu Leu Leu Trp Val Ser
1               5                   10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Ser Asn Gln Lys Asn Tyr Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Ser Tyr Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```